(12) United States Patent
Johnstone

(10) Patent No.: US 7,813,781 B2
(45) Date of Patent: Oct. 12, 2010

(54) METHOD AND APPARATUS FOR DETERMINING ISCHAEMIA

(75) Inventor: Alan John Johnstone, Aberdeen (GB)

(73) Assignee: Grampian Health Board, Aberdeen (GB)

( * ) Notice: Subject to any disclaimer, the term of this patent is extended or adjusted under 35 U.S.C. 154(b) by 664 days.

(21) Appl. No.: 10/524,228

(22) PCT Filed: Aug. 18, 2003

(86) PCT No.: PCT/GB03/03608

§ 371 (c)(1),
(2), (4) Date: Feb. 9, 2005

(87) PCT Pub. No.: WO2004/016162

PCT Pub. Date: Feb. 26, 2004

(65) Prior Publication Data

US 2006/0015025 A1    Jan. 19, 2006

(30) Foreign Application Priority Data

Aug. 16, 2002  (GB)  ................................. 0219068.4

(51) Int. Cl.
*A61B 5/05* (2006.01)
*A61B 5/00* (2006.01)
*A61B 5/02* (2006.01)

(52) U.S. Cl. .................... 600/361; 600/309; 600/483

(58) Field of Classification Search ............... 600/300, 600/301, 481, 483, 485, 486, 488, 561, 306, 600/309, 345, 361, 585

See application file for complete search history.

(56) References Cited

U.S. PATENT DOCUMENTS

| 3,224,436 | A |   | 12/1965 | Massena |   |
|---|---|---|---|---|---|
| 4,643,192 | A | * | 2/1987 | Fiddian-Green | 600/366 |
| 5,117,827 | A |   | 6/1992 | Stuebe et al. |   |
| 5,158,083 | A | * | 10/1992 | Sacristan et al. | 600/361 |
| 5,174,290 | A | * | 12/1992 | Fiddian-Green | 600/364 |
| 5,186,172 | A | * | 2/1993 | Fiddian-Green | 600/353 |
| 5,415,165 | A | * | 5/1995 | Fiddian-Green | 600/573 |
| 5,433,216 | A | * | 7/1995 | Sugrue et al. | 600/591 |
| 5,456,251 | A | * | 10/1995 | Fiddian-Green | 600/345 |
| 5,526,809 | A | * | 6/1996 | Fiddian-Green | 600/364 |
| 5,743,259 | A | * | 4/1998 | Kruse et al. | 600/309 |
| 5,766,432 | A | * | 6/1998 | Dunn et al. | 204/412 |
| 5,788,631 | A | * | 8/1998 | Fiddian-Green | 600/309 |

(Continued)

FOREIGN PATENT DOCUMENTS

WO    WO92/19150    11/1992

OTHER PUBLICATIONS

Heppenstall, R. Bruce: "The Compartment Syndrome", published in the journal "Clinical Orthopaedics and Related Research": No. 226, Jan. 1988, pp. 138 to 155.

(Continued)

*Primary Examiner*—Charles A Marmor, II
*Assistant Examiner*—Navin Natnithithadha
(74) *Attorney, Agent, or Firm*—Drinker Biddle & Reath LLP

(57) ABSTRACT

A method and apparatus for determining information concerning ischaemia using a pH sensor. Embodiments of the invention can be used to determine ischaemia caused by a number of factors, including acute compartment syndrome and vascular disorders, e.g. scepticaemia.

9 Claims, 24 Drawing Sheets

U.S. PATENT DOCUMENTS

| | | | |
|---|---|---|---|
| 5,813,403 A * | 9/1998 | Soller et al. | 600/310 |
| 5,848,965 A * | 12/1998 | Essen-Moller | 600/350 |
| 6,010,453 A * | 1/2000 | Fiddian-Green | 600/309 |
| 6,029,076 A * | 2/2000 | Fiddian-Greene et al. | 600/353 |
| 6,238,339 B1 * | 5/2001 | Fiddian-Greene et al. | 600/309 |
| 6,334,064 B1 * | 12/2001 | Fiddian-Green | 600/311 |
| 6,567,679 B1 * | 5/2003 | Khuri et al. | 600/345 |
| 6,600,941 B1 * | 7/2003 | Khuri | 600/345 |
| 6,766,188 B2 * | 7/2004 | Soller | 600/477 |
| 6,882,879 B2 * | 4/2005 | Rock | 600/547 |
| 6,965,795 B2 * | 11/2005 | Rock | 600/547 |
| 7,317,937 B2 * | 1/2008 | Phillips et al. | 600/310 |
| 7,373,195 B2 * | 5/2008 | Ye | 600/348 |
| 7,383,071 B1 * | 6/2008 | Russell et al. | 600/345 |
| 2002/0087057 A1 * | 7/2002 | Lovejoy et al. | 600/349 |
| 2003/0040665 A1 * | 2/2003 | Khuri et al. | 600/345 |
| 2003/0088163 A1 * | 5/2003 | Soller | 600/322 |
| 2004/0138542 A1 * | 7/2004 | Khuri et al. | 600/345 |
| 2005/0070769 A1 * | 3/2005 | Rock | 600/315 |
| 2006/0015025 A1 * | 1/2006 | Johnstone | 600/361 |

OTHER PUBLICATIONS

McKinley, Bruce A.: "Skeletal Muscle $P_{O2}$, $P_{CO2}$, and pH in Hemorrhage Shock, and Resuscitation in Dogs", published in "The Journal of Trauma": vol. 44, No. 1, pp. 119 to 127.

McKinley, Bruce A.: "Skeletal Muscle pH, $P_{CO2}$, and $P_{O2}$ during Resuscitation of Severe Hemorrhagic Shock", published in "The Journal of Trauma", vol. 45, No. 3, pp. 633 to 636.

* cited by examiner

Source of the Curve

— Reference Line

— moving ave. high ICP

...... absolute high ICP

Source of the Curve

— Reference Line

— moving average low dP

...... absolute low dP

METHOD AND APPARATUS FOR DETERMINING ISCHAEMIA

This Application is the U.S. National Phase Application of PCT International Application No PCT/GB03/003608 filed Aug. 18, 2003.

The invention relates to a method and apparatus for measuring intracompartmental pH, and especially but not exclusively to measuring intracompartmental and intramuscular pH for the diagnosis of ischaemia, and especially Acute Compartment Syndrome.

DESCRIPTION OF THE RELATED ART

Ischaemia is the reduction or cessation of blood flow to various parts of the body, leading to an insufficiency in local availability of the oxygen and metabolites normally carried by the blood. Ischaemia can arise locally from e.g. bone fractures causing local swelling in a limb which increases the distances between the cells and the arteries, thereby decreasing the effectiveness of the delivery of the oxygen and the metabolites from the blood. At the same time, the blood vessels are compressed due to the swelling, further reducing their capacity to deliver the nutrients and oxygen. Surgery also involves a risk of ischaemia, when blood vessels are severed during the procedure, either deliberately during the transplant of a free flap, or accidentally during the cutting procedure. Ischaemia can also arise chronically. Ischaemia can also arise from trauma at a remote site of the body. For example, a limb can become ischaemic when the blood flow is diverted from the limb back to the trunk of the body in response to central organ dysfunction or abdominal infection that could be remote from the site of ischaemia.

There are various kinds of ischaemia and among these Acute compartment syndrome (ACS) is a surgical emergency which if not recognised early may lead to crippling deformities, loss of limb or even death.

Compartment syndrome has been defined as "a condition in which increased pressure within a limited space compromises the circulation and function of tissues in that space"[1]. It is most commonly seen following injuries of the leg but may also occur in the upper limb, and following ischaemic re-perfusion injuries and burns. Furthermore, sub-clinical compartment syndromes have occurred following reaming of the medullary canal in the nailing of long bone fractures[2]. Early diagnosis and prompt surgical intervention is essential to avoid the complications which may ensue. These include neurological deficit, muscle necrosis, acute renal failure, amputation and loss of life. Currently, the diagnosis of acute compartment syndrome is based on clinical assessment and intra-compartmental (IC) pressure monitoring. Extreme pain exacerbated by passive stretching of the muscles in the compartment and paraesthesia are the most reliable signs, but may only become apparent in the later stages of acute compartment syndrome, and are not reliable in the unconscious, neurologically impaired or paediatric patient. In these circumstances invasive methods of monitoring IC pressure are therefore deemed essential[3].

Compartment pressure monitoring has been advocated since 1975[4]. There are a number of pressure monitors available but most rely on a column of fluid leading to inaccuracies.

BRIEF SUMMARY OF THE INVENTION

The invention also provides a method of determining the presence or severity of ischaemia in a tissue, the method comprising the steps of inserting a pH sensor into the tissue, and measuring the intracompartmental pH in the tissue.

Typically the tissue is muscle.

Typically, the method is used in the diagnosis of Acute Compartment Syndrome. Typically, the acute compartment syndrome is caused by a fractured limb.

The pH of muscle is a good indicator of its metabolic state with a normal physiological range of 6.95 to 7.2[5]. As the pressure in the compartment increases, blood flow ceases and lactic acid builds up, reducing the pH. By using a method of observing the changing pH of skeletal muscle tissue, it is possible to identify muscle which is at risk of irreversible damage prior to the development of clinical signs.

A second probe may also be provided to measure the intra-compartmental pressure; the pH and pressure measurements can be used in conjunction to provide a diagnosis.

Preferably, the or each sensor is mounted on a respective catheter. Preferably, the or each catheter is inserted into the muscle through a respective cannula.

Preferably, the or each cannula is inserted into skeletal muscle in an orientation that is generally parallel to the muscle fibres. Preferably, the or each cannula is inserted into the muscle adjacent to, but not communicating with, the fracture site.

Preferably, the or each sensor is monitored continuously for at least 24 hours.

Preferably, the reading from the or each sensor is compared with a calibrated scale to determine the extent of muscle damage. Typically, the reading from the or each sensor is used to determine the appropriate treatment, e.g., a fasciotomy. If the damage is caught early enough, a fasciotomy may be avoidable and intermittent pneumatic compression treatment or other conservative treatments may be sufficient.

According to a second aspect of the present invention, there is provided apparatus for determining the presence or severity of ischaemia, the apparatus including a pH sensor adapted to be inserted into a muscle.

Preferably, the apparatus is suitable for use in providing information concerning soft tissue, physiological changes and pathological conditions, such as septicaemia, pancreatitis and other blood disorders and conditions. Preferably, the apparatus is suitable for use in the diagnosis of Acute Compartment Syndrome.

Preferably, the pH sensor is mounted on a catheter. Typically, the catheter is glass-tipped.

Preferably, the glass is durable, heat-strengthened and fracture-proof.

Alternatively, the catheter is antimony-tipped.

The pH sensor and the pressure sensor can be mounted on the same catheter.

Optionally, the apparatus also includes a pressure sensor. Optionally, the pH sensor is connected to a pH recorder. Preferably, the pressure sensor is connected to a pressure monitoring system.

Typically, the pressure sensor is mounted on a second catheter. Alternatively, both the pH sensor and the pressure sensor are mounted on the same catheter. In this case, the pressure sensor and the pH sensor are preferably connected to the same monitoring system, which monitors and records both pressure and pH.

Optionally, two or more pH sensors are provided. Optionally, two or more pressure sensors are provided.

According to a third aspect of the present invention, there is provided the use of a pH sensor device for the determination of the presence or the severity of ischaemia and typically Acute Compartment Syndrome.

According to a fourth aspect of the present invention, there is provided a pH sensor device adapted to diagnose ischaemia, and typically Acute Compartment Syndrome.

The invention also provides a method of determining information concerning the condition of soft tissue, the method comprising the steps of inserting a pH sensor into the soft tissue and measuring the pH in the tissue.

According to the present invention, there is also provided a method of measuring intracompartmental pH, including the step of inserting a pH sensor directly into a muscle.

The method can be used to provide information about ischaemia arising from localised damage and remote trauma alike, as the pH measurement gives an accurate information about localised ischaemia, thereby allowing the method to be used for providing information about ischaemia arising from a wide variety of different causes.

BRIEF DESCRIPTION OF THE SEVERAL VIEWS OF THE DRAWINGS

An embodiment of the invention will now be described by way of example only and with reference to the following drawings, in which:—

DETAILED DESCRIPTION OF THE INVENTION

Figure 1:
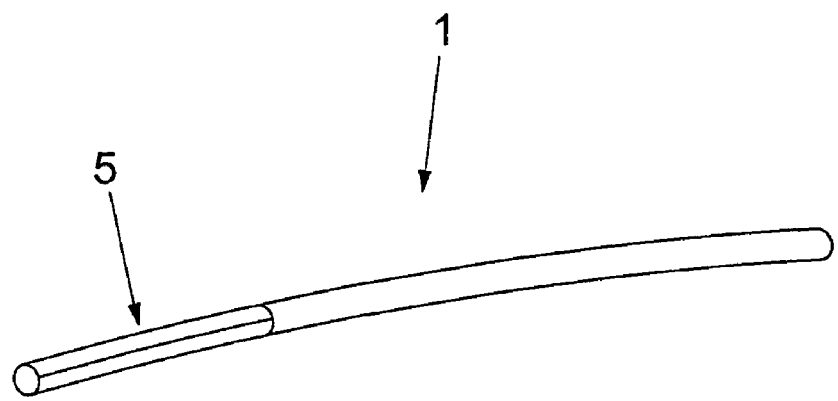
FIG. 1 shows a side view of a catheter with a pH monitor mounted thereon.

FIG. 1 shows a sterile 1.5 mm glass-tipped (Mettier Toledo) catheter 1 (made of durable, heat-strengthened, fracture-proof glass). A pH sensor probe 5 is mounted on the tip of the catheter 1. A glass pH catheter was chosen specifically for this study as these catheters have been shown to maintain a high accuracy of muscle pH recordings, with very little drift over time. They have no recorded ill effects and are easily sterilised to surgical standards as described below.

Figure 2:
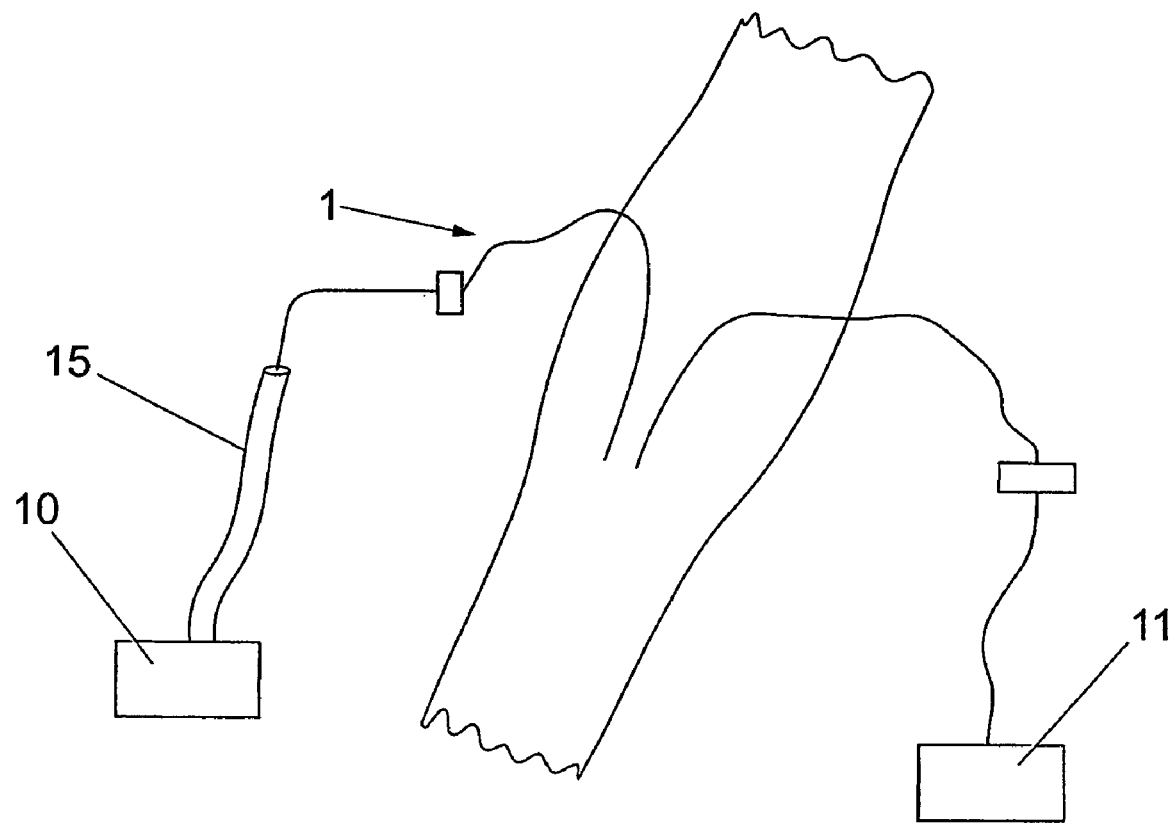
FIG. 2 shows a partial cross-section of a fractured limb, into which catheters with sensors are inserted.

FIG. 2 shows a portion of a lower leg of a patient into which is inserted the catheter 1 of FIG. 1. The catheter is inserted into skeletal muscle in the proximity of a fracture in the patient's tibia. The catheter 1 is connected to a pH recorder 10 via a sterilised adapter cable 15. A suitable pH recorder is the Flexilog 2010 dual-channel pH recorder (Oakfield instruments), which permits continuous monitoring of intracompartmental (IC) pH, accurate to one decimal place, at intervals of one second. The monitor also typically has a marker facility built in to allow events to be registered during the recording time.

FIG. 2 also shows a second catheter 2 connected to a pressure monitoring system 11, which is used to continuously monitor IC pressure. A suitable system is the Kodiag mobile pressure monitoring system (B Braun), which allows more accurate monitoring of pressure compared with other available devices[5], and is also easy to use and sterilise. The Kodiag monitoring system consists of a probe with a steel encased tip, which converts the pressure signal to an electrically useable signal, and is attached via an extension cable to the Kodiag measuring unit which then evaluates and displays the measured values. This system is capable of measuring pressure within a range of 0 to 199 mmHg, accurate to +/−1 mmHg.

General Methods

The pH unit is calibrated prior to each use. The unit has a calibration procedure built in which uses pH buffers of 7.0 and 1.1 to ensure that accurate readings are obtained with each individual. A circuit is created with the unit, the catheter, and the patient using an external reference electrode (ECG pad) and each buffer in turn. Following each patient's study, this circuit is re-created using the 7.0 buffer to obtain a reading, and therefore the value of any drift that has occurred during recording.

The pH probe and cable are sterilised to surgical standards, i.e. using a Tristel sterilisation bath. Further details of appropriate sterilisation procedures are given in the examples below.

The pressure probe is sterilised to surgical standards as per Kodiag instruction manual using steam sterilisation to a maximum temperature of 134° C.

The pH and pressure monitors are placed in the muscle through anaesthetised, surgically sterile skin. The catheters 1, 2 are inserted, typically through 14 gauge Adsyte intravenous cannulas placed generally parallel to the muscle fibres, and adjacent to each other, into the muscle compartment adjacent to, but not communicating with, the fracture site. The catheters should be inserted at a safe site, away from the position of impending incisions. The angle of insertion is typically approximately 30° to the skin.

If the apparatus is being used to diagnose suspected acute compartment syndrome caused by a tibial shaft fracture, the probes are typically inserted into the anterior compartment of the lower leg. For a femoral shaft fracture, the probes are typically inserted into the lateral portion of the anterior compartment of the thigh.

Upon penetration of the fascia in a distal direction, the catheter is levelled out and further advanced to its limit. The needle is then removed and the probe inserted through the lumen of the plastic sheath to a distance of approximately 1 cm beyond the tip of the sheath into the muscle belly. The probe and cannula are then typically secured with a clear adhesive dressing. The external reference electrode is then connected to the patient's limb, and both the pH probe and the external reference cable are then connected to the monitor and record mode 2 selected, at a desired measurement rate.

Optionally, other parameters may be measured simultaneously, for example blood pressure, oxygen saturation and end tidal carbon dioxide. Suitable recording devices for these parameters include the Critikon Dynamap 1846 SX, the Ohmeda Biox 3740 pulse oximeter, and the Captronic Ultra ETCO2 monitor respectively.

These parameters are measured at a desired interval, for example every five minutes. The blood pressure measurements allow "delta pressure" to be calculated (diastolic blood pressure minus IC pressure). A sustained delta pressure value of 30 mmHg or less is currently the most frequently used indicator for surgical intervention[4].

Intracompartmental pressure and pH are recorded continuously for at least 24 hours post-injury or for longer as clinically indicated. The marker facility is used as required, to record individual events during the recording time.

Following the completion of the measurements, both probes are removed, pressure applied to the puncture sites, and a small gauze dressing applied to the puncture wounds. Each probe is then wiped clean with a damp cloth ready for calibration. A post-recording calibration is then undertaken, which is identical to the calibration procedure prior to use.

The information collected is then downloaded into a software package, for example, the Flexisoft III software package, and the recorder's memory is then cleared, ready for future use.

After 25 uses, each pressure probe is returned to the manufacturers for recalibration, as recommended by the manufacturers.

EXAMPLE 1

The aims of this example were to demonstrate the ability of the pH monitor to record intramuscular pH in a situation of changing acidity resulting from tourniquet ischaemia, and the suitability and ease of use of the pH recorder in human skeletal muscle.

Over a period of five months, patients admitted to the elective orthopaedic unit of a local hospital were invited to participate. These comprised two groups, viz.:
1. elective knee arthroscopy (27)
2. elective total knee replacement surgery (12)

The pH monitor was calibrated on each patient in the ward prior to arrival in theatre. The pH probe and cable were sterilised to surgical standards in a Tristel 700 sterilisation bath. Five litres of Tristel 700 was mixed with 500 mls of activator in a sterilising bath once a week. When required, the probe was fully submerged in the bath for 10 minutes, as recommended in the Tristel guidelines. It was then rinsed in sterile water, and placed on a prepared sterile trolley ready for use.

Once general (or spinal) anaesthesia had been induced, a tourniquet was placed on the appropriate thigh (but not inflated), an external reference electrode was placed on the lateral thigh of the operative leg, and the surgical site was prepared and draped in a routine fashion.

The pH probe was inserted into the mid-portion of tibialis anterior of the appropriate leg, approximately 5 cm below and 1-2 cm lateral to the tibial tubercle. The probe was then connected to the Flexilog recorder and an interval of one second per measurement was selected. An initial end tidal carbon dioxide level was noted at this point (prior to tourniquet inflation) for the patients having a general anaesthetic. The leg was then elevated for three minutes and the tourniquet was subsequently inflated to 250-300 mmHg; the marker facility was used to mark the inflation of the tourniquet. Blood pressure, oxygen saturation and pH were then recorded at intervals of 5 minutes during the surgery.

After all of the measurements had been taken, the tourniquet was deflated. The marker facility was used to mark the deflation of the tourniquet. The probe remained in situ for 20 minutes after arthroscopy (Ax) and 30 minutes after knee replacement (TKR) after tourniquet deflation, during which time the muscle pH, blood pressure and peripheral oxygen saturation continued to be recorded at 5-minute intervals.

Following the end of recording and removal of the probe from each patient, the probe was checked to detect any drift in the system that had occurred during recording. This involved creating a circuit by the placement of the probe and the patient's finger in the 7.0 buffer, with the external reference electrode still connected to the thigh, and noting the recorded value at 1 minute.

EXAMPLE 2

A 26 year old male was admitted to the Intensive Therapy Unit following a road traffic accident, with generalised cerebral swelling and a closed fracture of his right tibia and fibula (Tscherne C3). Intra-compartmental monitoring of pH, ICP and monitoring of diastolic blood pressure within the right tibialis anterior began 11 hours post injury prior to transfer to theatre for intramedullary nailing. Clinically, the leg appeared very swollen and tight, but no subjective data was available as he was ventilated and sedated for his head injury. Following intramedullary nailing of the tibial fracture, concern was raised as to the presence of ACS, and ICP monitoring had revealed a delta pressure (diastolic blood pressure—ICP) of 30 or less prior to, and throughout his surgery (current guideline for diagnosis of ACS). Full four compartment fasciotomies were performed and bulging, boggy muscle was revealed, with some dark areas of muscle suggesting ischaemia. On return to theatre 48 hours later, the muscle appeared healthy, several small open biopsies were taken, and the wounds were closed with split skin grafts. Clinically he had no residual signs or symptoms attributable to ACS at his 8 week follow up appointment.

EXAMPLE 3

A 19 year old male sustained an open fracture of the left tibial shaft (Gustilo I) when he was knocked off his pedal bike. Monitoring of muscle pH, ICP and diastolic blood pressure commenced in theatre following anaesthesia and wound debridement following the method described above, to maintain sterility.

EXAMPLE 4

Over approximately six months, patients admitted to a local hospital, with a fracture involving the diaphysis of the tibia or femur, a crush injury, or a suspected compartment syndrome at any anatomical site, were invited to take part in this study. All patients suffering from the above injuries during the study period were approached to take part, subject to fulfilling ethical entry criteria. Subjects underwent intra-compartmental monitoring of pressure and muscle pH for up to 48 hours. In addition, muscle biopsies were obtained from those patients having a surgical procedure under general anaesthesia. Information pertaining to patient demographics, current injury, and relevant past medical history was collected from their casualty cards, medical notes and radiological investigations.

The trauma group included 61 patients admitted to the orthopaedic unit/intensive care unit, suffering from one or more of the following injuries:
1. Tibial shaft fractures
2. Long bone fractures of the lower limb requiring intramedullary nailing
3. Acute compartment syndrome, at any anatomical site, diagnosed by the patient's medical team with currently accepted methods
4. Crush injuries As the admission of trauma patients is not as predictable as elective admissions, and cold sterilising techniques were not regularly used in the trauma theatre, the pH probe and cable were sterilised in a Tristel One Day concentrate bath. On each occasion requiring the use of the sterilisant, 25 mls of each liquid were mixed with 950 ml of plain tap water. A tester kit was used to ensure an effective sterilisant was produced and the probe was submerged for the recommended 5 minutes. The solution was then discarded after only one use.

The pH and pressure probes were inserted into the appropriate muscle compartment within 5 cm of, but not communicating with, the fracture site/within the site of the crush injury. If the probes were placed prior to fracture fixation, they were inserted within a long sterile plastic bag, to ensure continuing sterility of the wider surgical field during the ensuing procedure. The Flexilog system was set up to record pH at six second intervals to allow recording to continue for up to 96 hours.

The probes were introduced parallel to each other in adjacent sites within the same fascial compartment: the anterior compartment of the lower leg for tibial fractures; the lateral compartment of thigh for femoral fractures, and the appropriate site for suspected compartment syndromes at other anatomical regions. In those patients who were not undergoing a general anaesthetic in the next few hours, a local anaesthetic used to anaesthetise the skin alone was used at the site of cannula entry. Once compartment monitoring commenced, the ICP, muscle pH, blood pressure and peripheral oxygen saturation were recorded at 5 minute intervals during surgery, then hourly for the duration of the study. For those patients treated with a Plaster of Paris cast, the probes were inserted under local anaesthetic (as above), prior to the application of a full leg cast, and a window was created in the plaster over the probe site to allow removal of the probes upon completion of the studies.

For those with tibial and femoral shaft fractures treated with intramedullary nails, a further protocol was introduced during the operation. The marker facility was used to mark those events during surgery which were related to fracture fixation and fasciotomies. All parameters were recorded on the patient's chart at the following points:
1. Pre-anaesthetic
2. Post-anaesthetic
3. Traction application
4. Guidewire insertion
5. Reaming of the medullary canal
6. Intramedullary nail insertion
7. Post nail insertion
8. Fracture impaction
9. Post-traction release
10. Recovery room For those patients suspected clinically of having a compartment syndrome and taken to theatre for fasciotomies, the marker facility was used to mark the following events:
1. Induction of anaesthetic
2. Appropriate skin and fascial incisions
3. Decompression of each compartment (4)
4. Recovery Blood pressure and peripheral oxygen saturation were monitored. During anaesthetic time using an endotracheal tube or laryngeal mask, the patient's end tidal carbon dioxide (ET $CO_2$) was recorded.

During their stay in hospital, all of the patients were regularly assessed clinically for evidence of pain on passive stretch, muscle weakness and sensory changes in the injured limb to identify the presence of a developing acute compartment syndrome. In addition, all of the patients who underwent fasciotomies for suspected compartment syndrome, had a clinical intra-operative assessment of muscle damage performed and recorded. This included visualisation of the state of the muscle within the compartment as the fascia was incised, with colour, obvious bulging, oedema, necrosis and muscle twitch response recorded appropriately.

EXAMPLE 5

This example examines an ischaemic mammalian muscle model, to review and compare the underlying biochemistry, immunocytochemistry, and histochemistry of muscle ischaemia to muscle pH measurements, to verify the intramuscular (IM) pH readings, and to identify "critical pH" levels for skeletal muscle, beyond which point irreversible tissue damage occurs.

METHODS FOR EXAMPLE 5

Male rats were sacrificed through stunning and neck fracture and Ischaemia time was noted. They were placed in an incubator, maintained at 37° C. The quadriceps femoris muscle was exposed atraumatically and a 1.5 mm diameter, glass tipped, single channel pH catheter (M1.5; M.I.C. France), connected to a 2020 Flexilog pH monitor (Oakfield Instruments, UK) was employed to monitor muscle pH. This system required an Ag/AgCl external reference probe. Before and after use the monitor was calibrated at pH 1.1 and pH 7, and drift was found to be minimal. The pH catheter was cleaned between usages with an alcohol-based solution, and prior to use was thoroughly irrigated with saline. Following exposure of the quadratis femoris muscle, the pH catheter, through a 12 gauge cannula and the external reference probe were inserted into the exposed muscle belly. At predetermined pH levels muscle biopsies were taken under direct vision. These samples were snap frozen in liquid $N_2$. The samples were stored at −80° C., prior to freeze-drying. A commercially available freeze-drier was used and the samples stored in a desiccator at −10° C.

Immediately prior to analysis, the samples were pulverised with an agate pestle and mortar and the connective tissue was removed. The remaining muscle powder was thoroughly pulverised and two 10 mg samples were weighed into disposable plastic centrifuge tubes for extraction and analysis.

Muscle metabolites were extracted with cold 0.5 N perchloric acid containing 1 mmol/l EDTA at a ratio of 1 ml perchloric acid for every 12.5 mg of muscle powder. This solution was agitated in an ice bath for ten minutes and then centrifuged for 60 seconds. The supernatant was removed and neutralised by the addition of a one-fourth volume of 2.1 mol/l $KHCO_3$.

Assays

The concentrations of Glucose-6-Phosphate (G6P), Lactate and Pyruvate, expressed as millimoles per kilogram of dry muscle were assayed by modifications of the method of Olsen[8]. Fluorometric measurements were made on a filter fluorimeter (Locarte model LF 8-9: Locarte, London, UK). All fluorimetric analyses were conduced using standard solutions that had been calibrated photometrically.

Glucose-6-Phosphate was assayed in the presence of 100 mmol/l Tris buffer, pH 8.1; 5 mmol/l NADP; and G-6-P Dehydrogenase, 10 U/ml.

Lactate was assayed in the presence of 1.1 mol/l Hydrazine buffer, pH 9.0; 5 mmol/l NAD; and Lactate Dehydrogenase, 2750 U/ml.

Pyruvate was assayed in the presence of 0.5 mol/l Phosphate buffer, pH 7.0; 2 mmol/l NADH; and Lactate Dehydrogenase, 5.5 U/ml.

In each case the reaction mixture containing buffer, cofactor and enzyme was prepared immediately prior to use. By keeping the reaction volume small, favourable kinetics were ensured. All incubations were carried out at room temperature, samples and standard solutions being treated identically.

At the end of the incubation period the sample was diluted by the addition of 1 ml of $H_2O$. The fluorescence was then read; for G6P and lactate the blank was set to zero; for pyruvate the highest standard solution was set to zero. Sample values were obtained by comparison with the standard curve and the corrected for the dilutional effects of the extraction. ATP and PCr were assayed using modifications to the original methods described by Harris[7]. Spectrophotomic measurements were made on an Epperdorf photometer (Model 1101M, wavelength=334 nm).

ATP and PCr were assayed sequentially in the presence of 50 mmol/l TEA buffer, pH 7.5; 0.1 mol/l Magnesium Chloride; 0.5 mol/l Glucose; 22 mol/l ADP; 5 mmol/l NADP; G6P Dehydrogenase, 10 U/ml; Hexokinase, 50 U/ml; and Creatine Kinase 90 U/ml.

Analysis of ATP and PCr were made on the same day as extraction.

EXAMPLE 6

The aim of this example was to demonstrate the ability to monitor the muscle pH changes associated with limb ischaemia, in both the acute and the chronic forms. In vascular surgery there are a number of novel uses for pH monitoring including assisting in the decision to re-vascularise compromised limbs or to primarily amputate to avoid the potentially life threatening systematic effects of re-vascularistion.

The calibration, sterilisation and insertion techniques used in this study were identical to those described above in the method section. Markers were used in this instance during surgery for clamping of the artery (ON), release of the clamp (OFF), return to full circulation (CIRC) and in some cases, during the angiogram (ANGIO) used to check graft patency.

RESULTS FOR EXAMPLE 1

The following analyses were conducted on the results from a subgroup of the patients; 24 patients undergoing elective knee surgery and 8 patients undergoing elective total knee replacement surgery.

Arthroscopy Study Group

This example covered eighteen men and seven women (mean age of 41 years, mean tourniquet time of 21 minutes). The mean muscle pH before the tourniquet was inflated was 6.9. This decreased by 0.3 to 6.6 prior to the tourniquet being released. Fifteen minutes after the tourniquet was deflated the muscle had recovered by an average of 0.16 of a pH unit to 6.76.

Figure 3A:
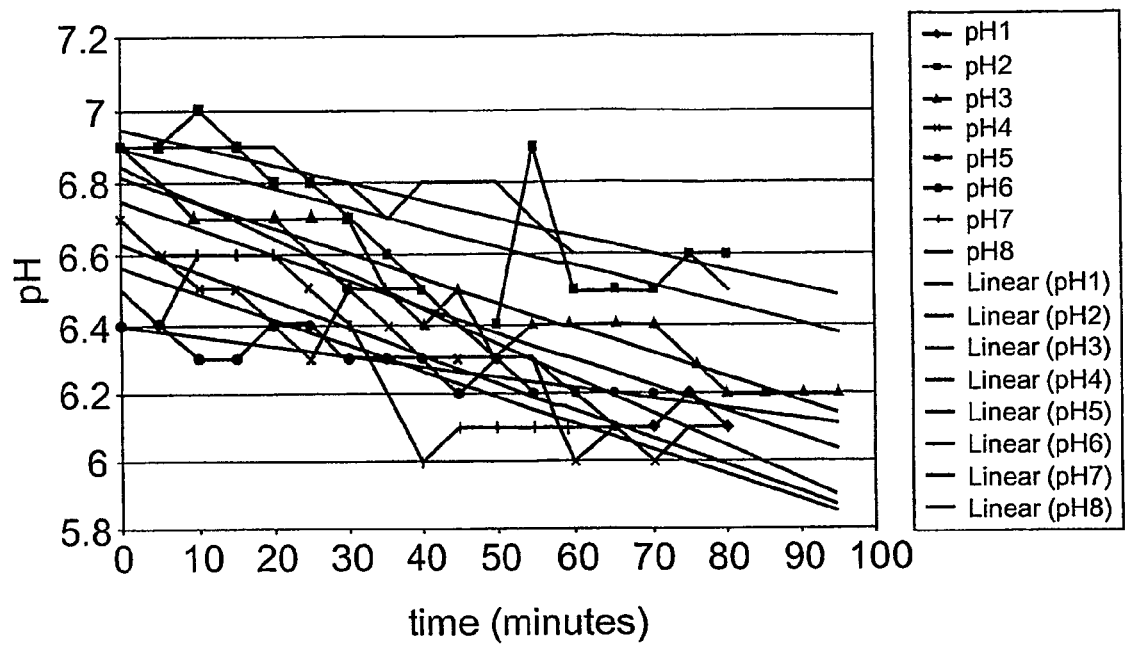
FIG. 3a shows a graph of pH as a function of time for the total knee replacement surgery group of example 1 during tourniquet inflation.
Figure 4A:
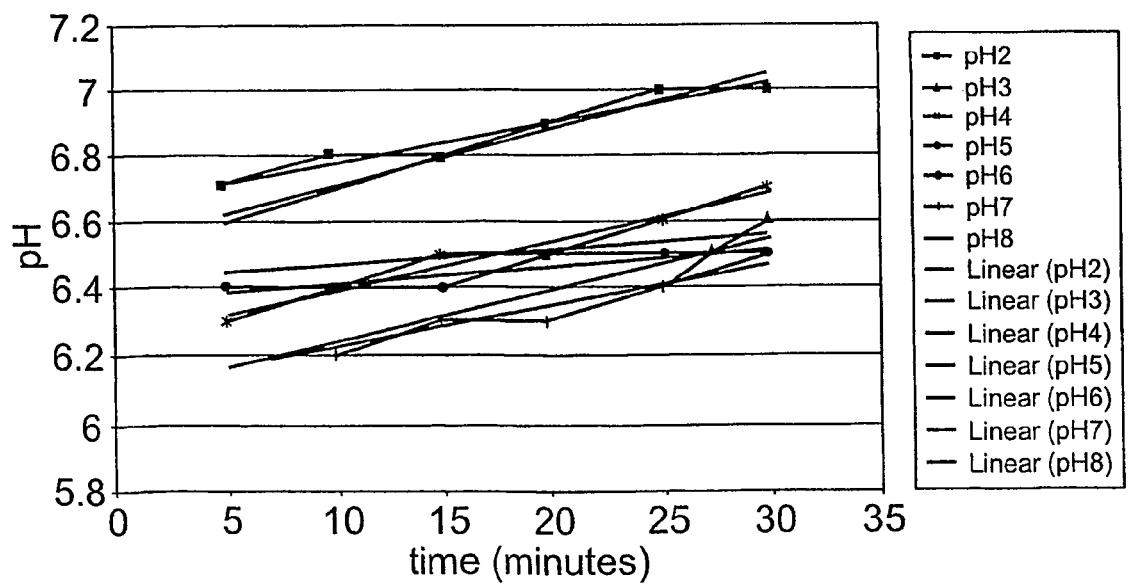
FIG. 4a shows a graph of pH as a function of time for the total knee replacement surgery group of example 1 following release of tourniquet.
Figure 3B:
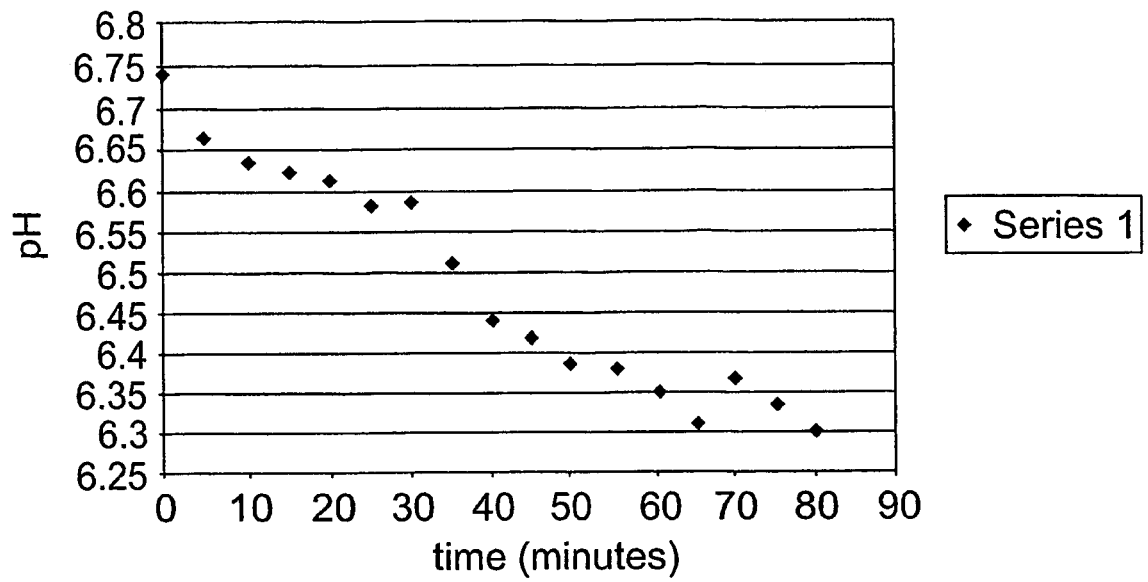
FIG. 3b shows a graph of the mean pH changes from the FIG. 3a graph.
Figure 4B:
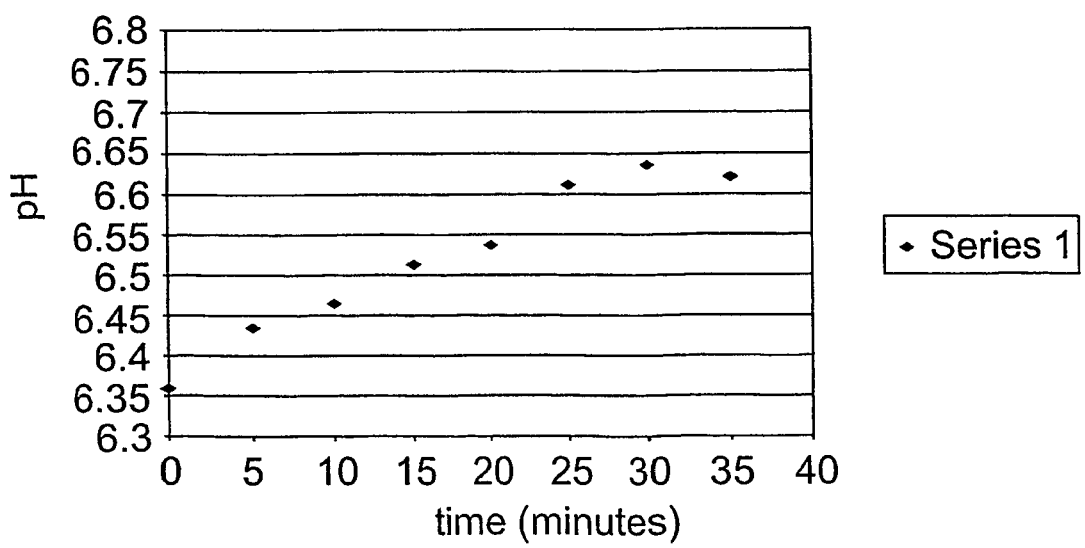
FIG. 4b shows a graph of the mean pH changes from the FIG. 4a graph.

Total Knee Replacement Study Group (see FIGS. 3 and 4).

This group of patients included 3 males and 5 females (mean age of 68 years, mean tourniquet time of 79 minutes). The mean pH prior to tourniquet inflation was slightly lower than the arthroscopy group at 6.7, and decreased to 6.2 before the tourniquet was released. Fifteen minutes later, muscle pH had recovered by 0.28 of a pH unit to 6.48, with further recovery of 0.16 to 6.64 by 30 minutes (total recovery of 0.44).

The average pH recorded prior to release of the tourniquet in the knee replacement group was 6.3.

The remaining analyses of Example 1 cover the full group of 27 patients undergoing elective knee arthroscopies and 12 patients having total knee replacements.

Statistical analysis of the results was completed using SPSS for windows, version 10.0 (Microsoft). Non-parametric statistical tests were used due to the skewed distributions of the samples. For correlations between continuous data, Spearman's rho correlations were employed. For comparisons of categorical data with continuous data, Mann-Whitney tests were used. When looking for significant changes over time, Wilcoxon matched pairs testing was carried out.

Table 1.1 shows the general descriptive data gathered for Example 1. The group has been sub-divided into two sets, those who underwent knee arthroscopy, and therefore had a relatively short period of tourniquet ischaemia, and those who had total knee replacement surgery (TKR), and therefore required prolonged use of the tourniquet.

TABLE 1.1

General descriptive data

| Category | Whole Group N = 39 | Arthroscopy n = 27 | TKR N = 12 |
|---|---|---|---|
| Male | 25 | 19 | 6 |
| Female | 14 | 8 | 6 |
| Mean Age (years) | 48 | 40 | 68 |
| Mean Tourniquet time (minutes) | 37 | 21 | 74 |
| Tourniquet Pressure 300 mmHg | 33 | 21 | 12 |
| Tourniquet Pressure 250 mmHg | 6 | 6 | 0 |

Figure 9:
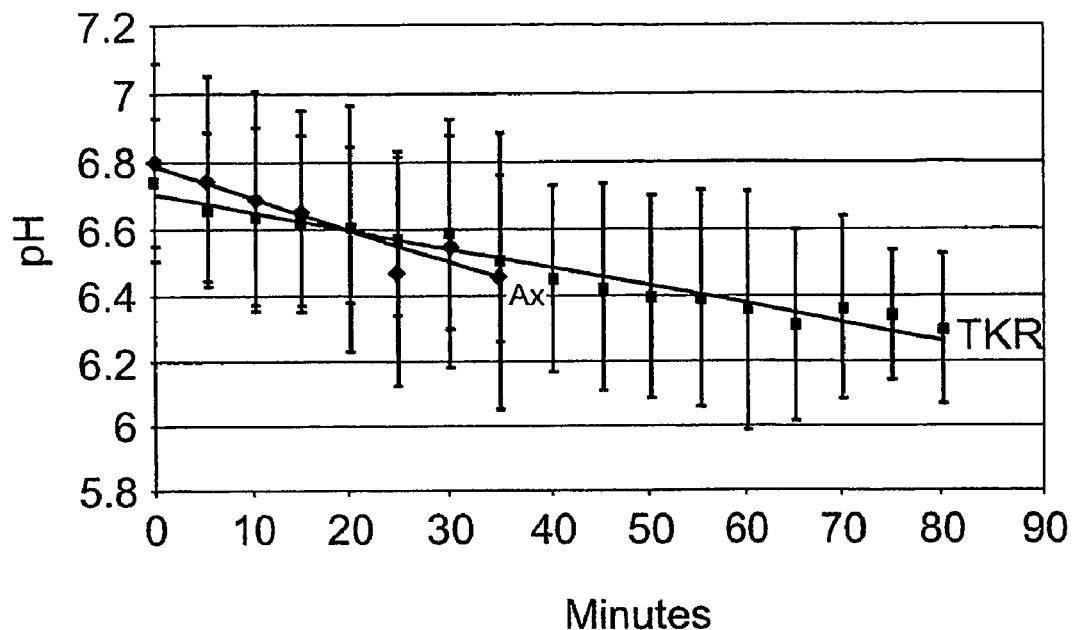
FIG. 9 shows a graph of pH against time for example 1 upon inflation of the tourniquet.

The mean change in pH during tourniquet ischaemia for each sub-group is displayed in FIG. 9. In the arthroscopy (Ax) group, the mean muscle pH prior to tourniquet inflation was 6.80. This decreased to 6.58 prior to the tourniquet being released, and recovered to 6.66 in fifteen minutes. Although the mean pH prior to tourniquet inflation was slightly lower in the total knee replacement (TKR) group (6.74), the difference was not statistically significant (table 2). However, the pH decreased to 6.35 prior to tourniquet release in the knee replacement group, which was significantly different from the arthroscopy group (table 1.2). Fifteen minutes after tourniquet release, the muscle pH in the TKR group had recovered to 6.51, with further recovery to 6.63 by 30 minutes. In the whole group, recovery to baseline pH was achieved within 30 minutes following release of the tourniquet ($z=-1.232$; $p=0.218$).

Using the whole group, several factors, including age, gender, initial end tidal carbon dioxide, and the tourniquet inflation pressure, were analysed as to their effects on either the baseline muscle pH recorded prior to tourniquet inflation, the change in pH occurring during tourniquet ischaemia, or during recovery (Table 1.2). No one factor had a significant influence on the results.

TABLE 1.2

The effect of various factors on the initial pH, and changes in pH occurring during ischaemia and recovery

|  | Age* | Gender† | Surgery† | Tpressure† | ETCO2* | Side† |
|---|---|---|---|---|---|---|
| Baseline Ph | cc 0.063<br>p = 0.720 | Z = −0.511<br>P = 0.609 | z = −0.901<br>p = 0.368 | z = −1.696<br>p = 0.090 | cc = 0.112<br>p = 0.650 | z = −1.167<br>p = 0.243 |
| Ischaemic pH change | cc = −0.237<br>p = 0.159 | Z = −0.840<br>P = 0.401 | z = −3.034<br>p = 0.002** | z = −0.725<br>p = 0.468 | cc = 0.152<br>p = 0.524 | z = −0.201<br>p = 0.841 |
| Recovery 0-15 minutes | cc = −0.009<br>p = 0.961 | Z = −0.218<br>P = 0.827 | z = −0.847<br>p = 0.397 | z = −0.669<br>p = 0.504 | cc = 0.082<br>p = 0.731 | z = −0.699<br>p = 0.484 |
| Recovery 15-30 minutes | cc = −0.222<br>p = 0.595 | Z = −0.833<br>P = 0.405 |  |  | cc = 0.949<br>p = 0.051 | z = −1.725<br>p = 0.084 |

*Spearman's rho correlations cc = correlation coefficient
†Mann Whitney tests
**Significant to the 0.01 level The mean recorded value in the drift measurement was 7.07 (SD 0.28) for the whole group, which does not represent a significant drift during recording ($z=-1.211$, $p=0.226$).

It was found that placement of the external reference electrode close to the probe insertion site resulted in the best recordings.

The pH decreased during the period of tourniquet inflation and recovered upon release.

Statistical analysis revealed a linear pattern of pH decline upon inflation of the tourniquet (FIG. 9). Furthermore, Wilcoxon ranked pairs testing found no significant differences between the reduction in pH for each 5-minute interval during this trial. The change in muscle pH was significant following just 5 minutes of tourniquet ischaemia ($p<0.001$).

Figure 10:
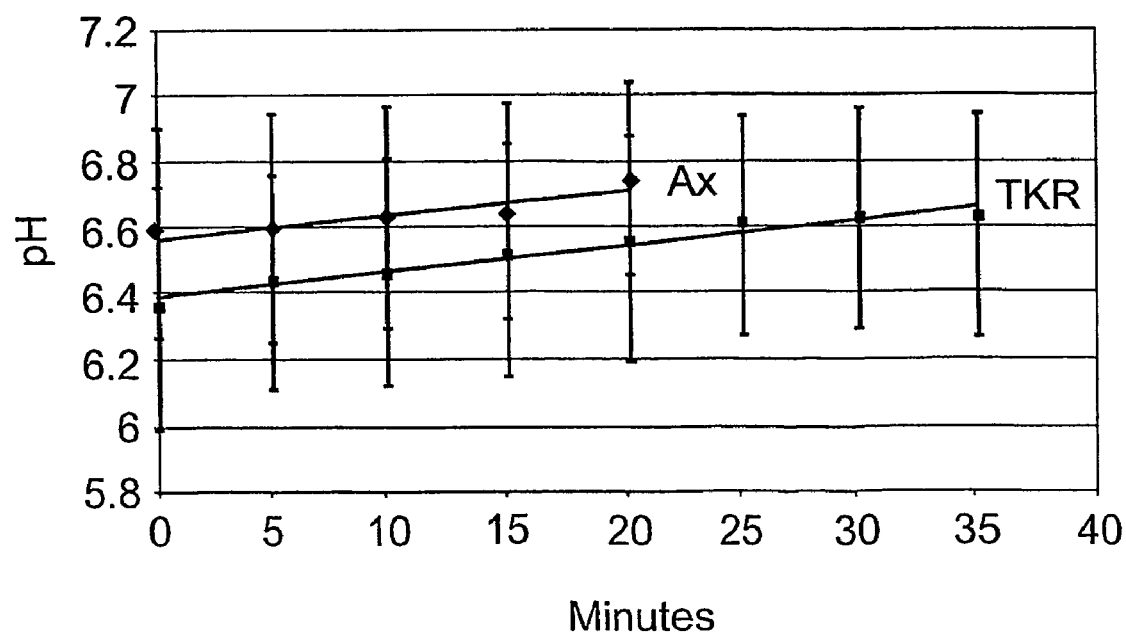
FIG. 10 shows a graph of pH against time for example 1 upon deflation of the tourniquet.

Upon release of the tourniquet, the intramuscular pH increased (FIG. 10). However, it remained significantly different from baseline pH values until 20 minutes after the tourniquet was removed in the arthroscopy group, and 25 minutes of re-perfusion in the knee replacement group. This is thought to reflect the prolonged tourniquet time in the latter group.

The pH monitor chosen for this study was easy to use, acceptable to patients, and recorded pH intramuscularly. It was therefore deemed acceptable for use.

RESULTS FOR EXAMPLE 2

Figure 5:
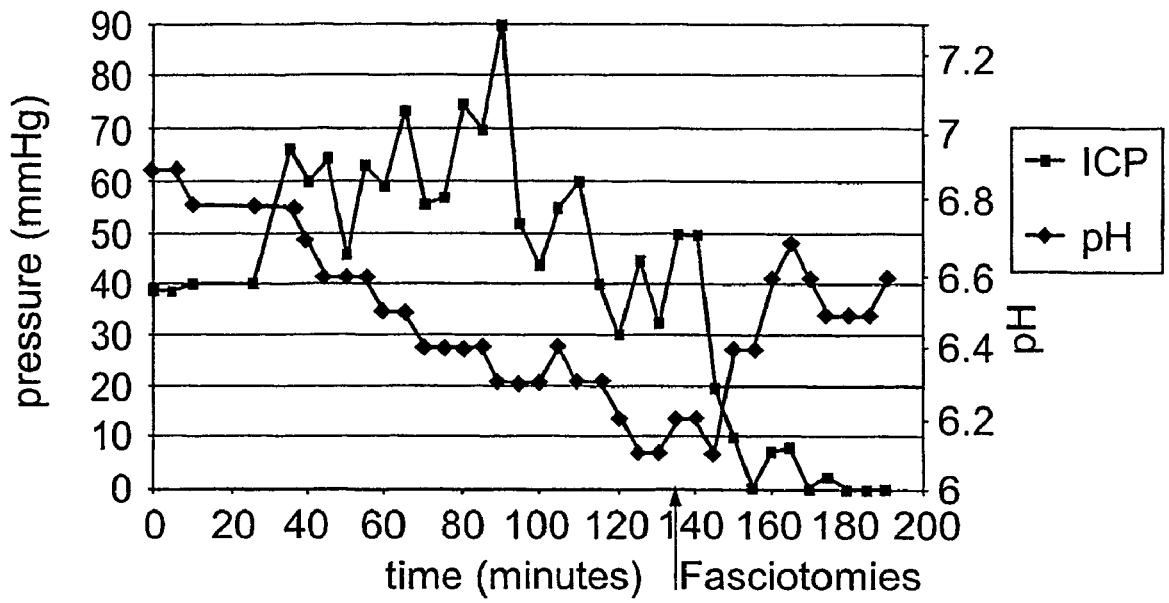
FIG. 5 shows a graph of pH and intracompartmental pressure as functions of time for a patient with Acute Compartment Syndrome undergoing Intramedullary Nailing.
Figure 7:
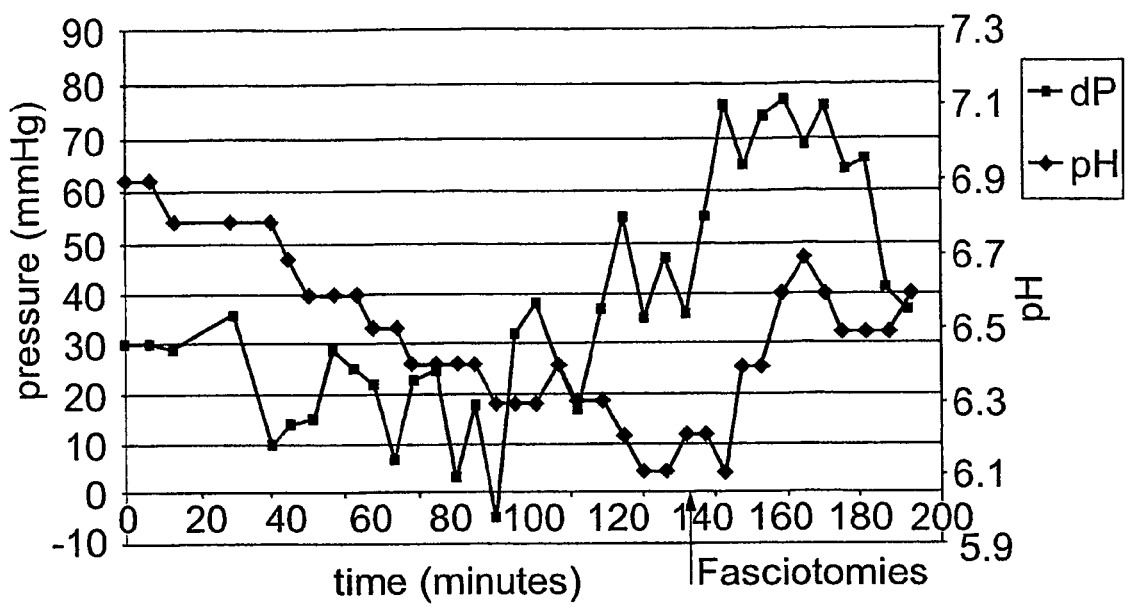
FIG. 7 shows a graph of pH and delta pressure (diastolic blood pressure minus IC pressure) as functions of time for the patient of FIG. 5.

The pH and absolute intracompartmental pressure (ICP) readings during theatre have been plotted on the graph shown in FIG. 5, while FIG. 7 shows pH results compared with the delta pressure recordings. It is clear that the muscle pH reduced significantly during sustained high ICP, and recovered following fasciotomies.

RESULTS FOR EXAMPLE 3

Figure 6:
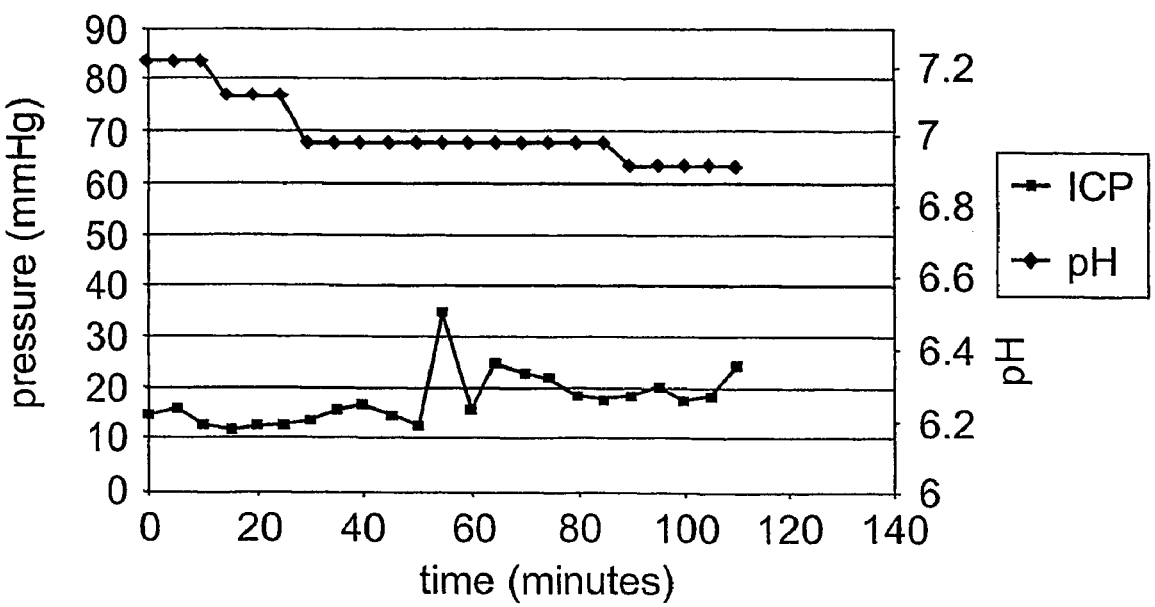
FIG. 6 shows a graph of pH and intracompartmental pressure as functions of time for a patient who did not have Acute Compartment Syndrome undergoing Intramedullary Nailing.
Figure 8:
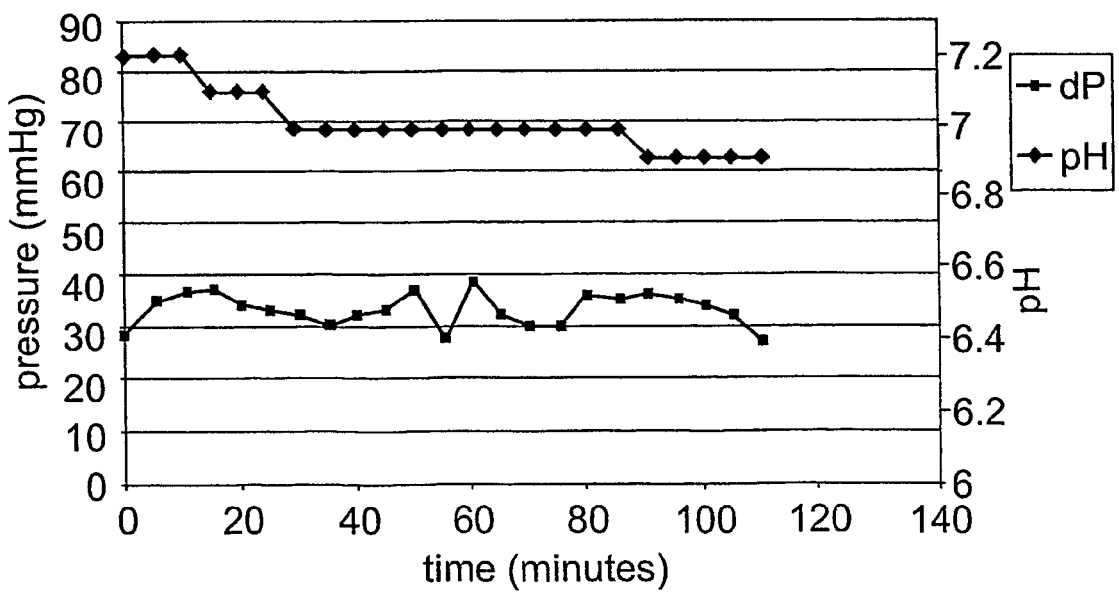
FIG. 8 shows a graph of pH and delta pressure (diastolic blood pressure minus IC pressure) as functions of time during Intramedullary Nailing for the patient of FIG. 6.

The results can be seen in FIGS. 6 and 8. The muscle pH remained in the physiological range throughout the operation, while neither the absolute ICP, nor the delta pressure met the current criteria for diagnosing ACS. At no point did the patient show any signs of impending or missed ACS.

RESULTS FOR EXAMPLE 4

Sixty one patients admitted to the Orthopaedic Trauma Unit fulfilled the inclusion criteria and agreed to participate in the study. Of this group, pH was successfully recorded in 60 patients. Pressure was also omitted in one patient following damage to one of the probes. Twenty nine (48%) patients have been seen for their six and/or 12 month follow up appointments to date.

The full group was further subdivided into patients who were deemed to have an acute compartment syndrome (ACS), and those who did not (normal). Patients were included in the ACS group in one of two ways. They were either diagnosed with ACS via clinical assessment and/or pressure measurements by the surgical team, and therefore underwent fasciotomies during their hospital stay, or they were found to have clinical signs of a previous compartment syndrome at subsequent follow up appointments. The median age for each group was similar, and the majority of the patients were male (82%), particularly in the ACS group (94%).

All three variables, pH, ICP and delta pressure, were recorded for up to 48 hours starting as soon as possible following the patient's injury. The median time from injury to monitor insertion was 11 hours (interquartile range 8.2, 17.7), with a median delay to surgery of 14.5 hours (iq range 7.2, 20). The mean recordings obtained for ICP, dP and pH are displayed in FIGS. 11 to 13 respectively.

Figure 11:
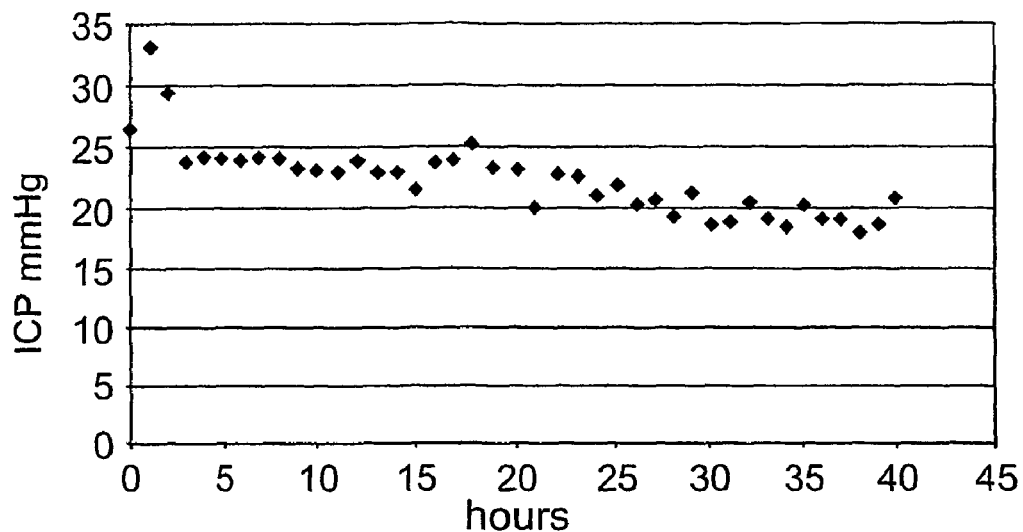
FIG. 11 shows a graph of ICP against time following injury for example 4.
Figure 12:
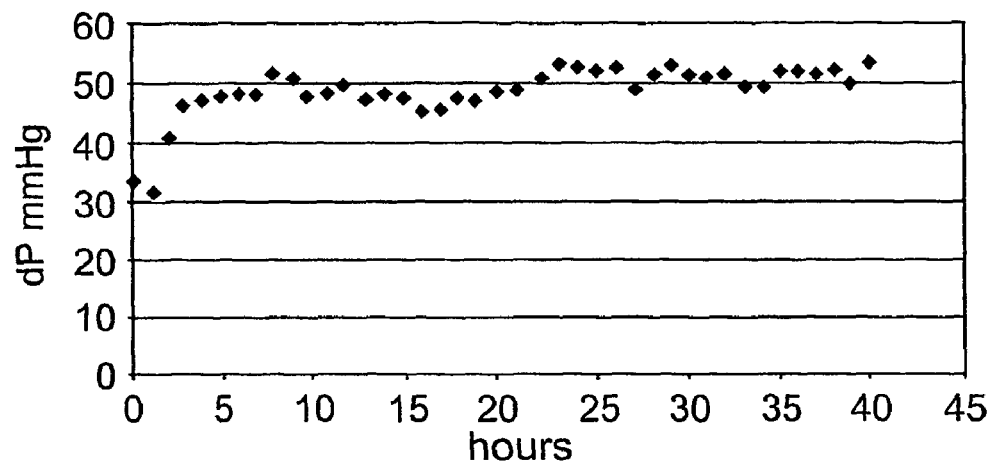
FIG. 12 shows a graph of delta pressure against time following injury for example 4.
Figure 13:
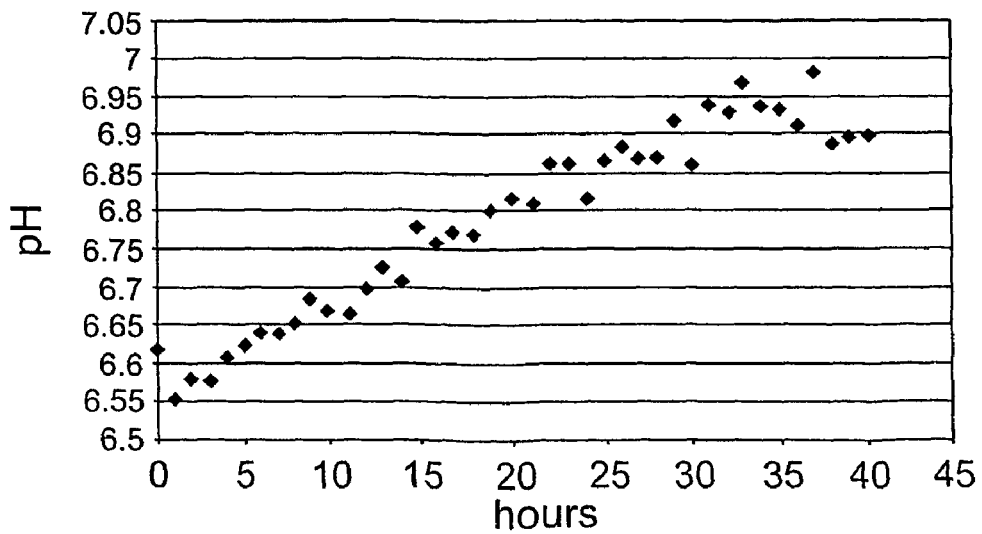
FIG. 13 shows a graph of intramuscular pH against time following injury for example 4.

FIGS. 11 and 12 show a clear elevation in ICP and a drop in delta pressure (dp) during the first 2 hours of recording. This is followed by a steady, slow recovery over the next 38 hours. Sixty one percent of the whole group suffered a tibial shaft fracture that was treated with IM nailing. This procedure caused high peaks in intra-compartmental pressure, particularly during reaming and nail insertion, which may be at least partly responsible for these initial values.

The pH (FIG. 13) shows a linear pattern of recovery subsequent to an initial drop, and prior to flattening of the curve once normal values are reached (>6.9).

In order to simplify the analysis of the large quantity of data obtained during this study, the "worst" hourly values of each variable were calculated for each patient. Although this was straightforward for pH measurements, some difficulty was encountered regarding the pressure-based recordings. Those patients who underwent IM nailing experienced many very high peaks in compartment pressure (up to 140 mmHg) as a result of reaming and nail insertion, however they were generally not sustained. For some of the readings, the hourly recording fell within the time during the nailing, and therefore the values appear artificially inflated (highest ICP (HICP), lowest dP (LDP)). To compensate for this, moving hourly averages were calculated during IM nailing, to give a better indication of the overall state of the pressure within the compartment (ave. ICP, ave. dP). However, both sets of data were analysed, to ensure that these peaks did not significantly alter the results.

In order to ensure the accuracy of the recordings obtained throughout each patient's study, both the pH and pressure systems were tested for accuracy upon completion of the study, and therefore any drift that had occurred was detected (see table 3). The drifts in each system were not significantly different between the ACS and normal groups.

TABLE 4.1

Drift in systems during monitoring: ICP monitor in air (0), and pH monitor in 7.0 buffer

|  | Full group | | ACS | | Non ACS | | P |
|---|---|---|---|---|---|---|---|
|  | Median | Iq range | Median | Iq range | Median | Iq range | value |
| ICP | 0.00 | 0, 1.5 | 0.00 | 0, 4 | 0.00 | 0, 0.75 | 0.398 |
| pH | 7.2 | 7.025, 7.35 | 7.1 | 7.0, 7.35 | 7.2 | 7.10, 7.38 | 0.537 |

Intramedullary Nailing of the Tibia

Thirty-seven patients underwent IM nailing of the tibia, with a mean procedure time of 96 minutes (SD 21.62).

Figure 14:
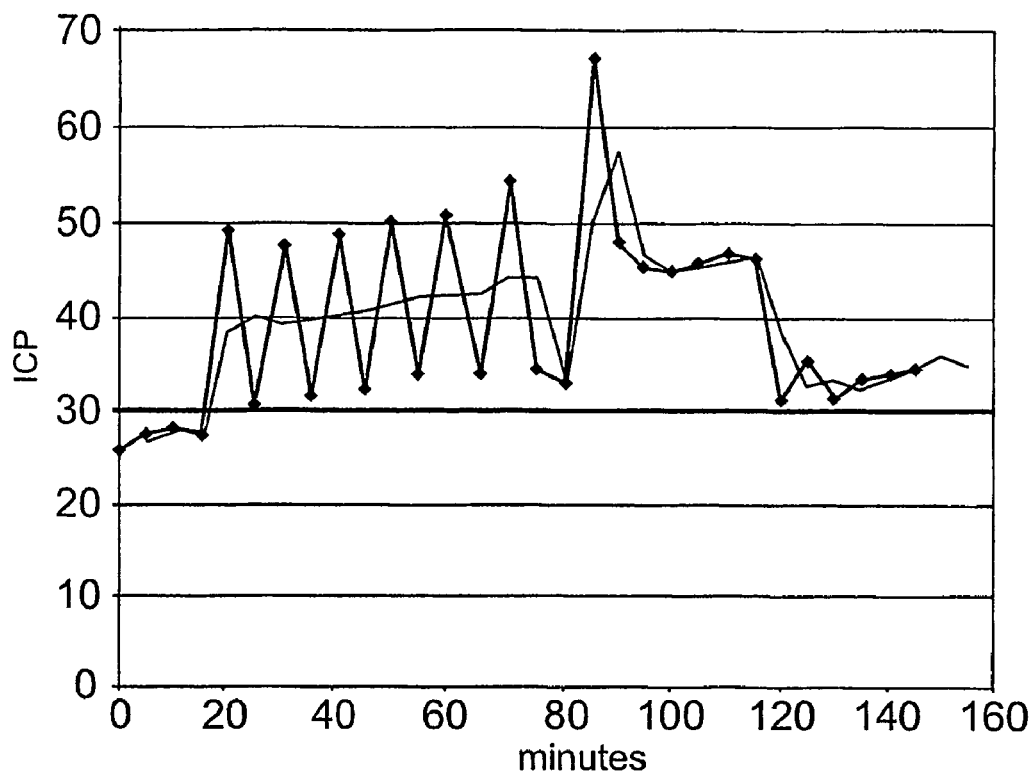
FIG. 14 shows a graph of ICP against time for the patients of example 4 undergoing intramedullary nailing.
Figure 15:
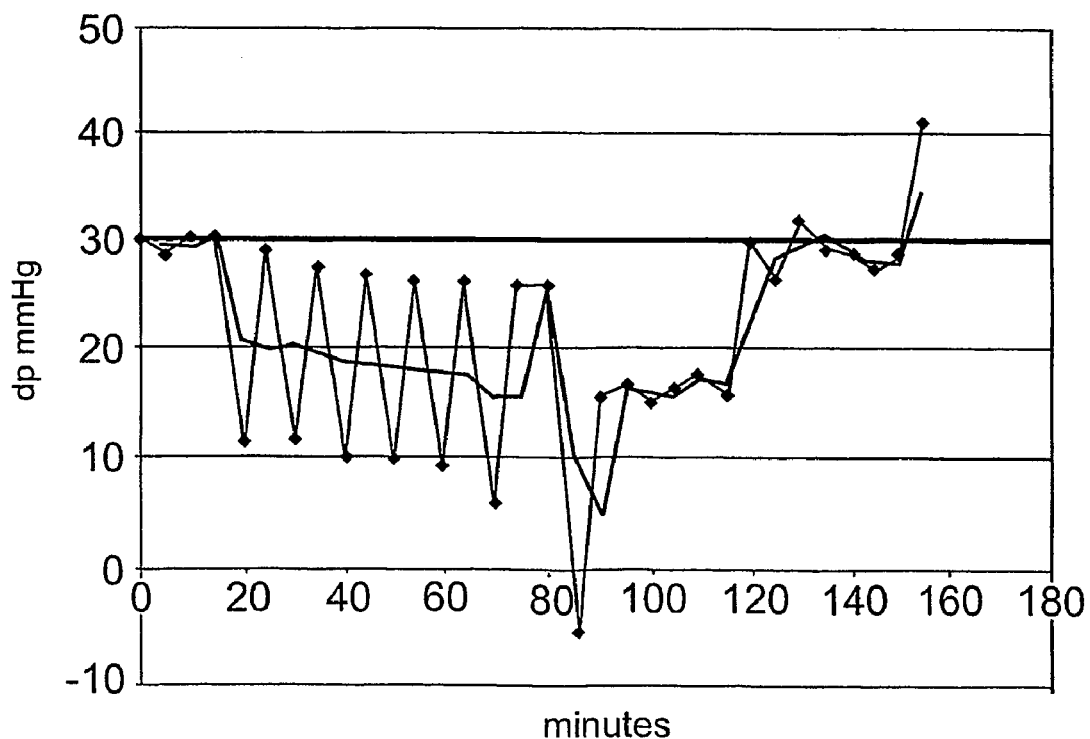
FIG. 15 shows a graph of delta pressure against time for the patients of example 4 undergoing intramedullary nailing.

During IM nailing, recordings before, during and after each event were recorded. These results were used to produce graphs representative of the average patient in terms of both time and each event (see FIGS. 14 and 15). These show high peaks in pressure during guidewire insertion, reaming and nail insertion, with a sustained elevation in absolute pressure following nail insertion. The current criteria for ACS (ICP>30 mmHg, delta pressure<30 mmHg) are marked on the graphs.

Acute Compartment Syndrome

For the purposes of this study, the ACS group included all those patients who were diagnosed with ACS during their in-patient stay using clinical parameters and/or pressure studies (n=12). Clinical follow up at 6 and 12 months further identified those with evidence of a previous compartment syndrome (n=4). All patients were then included in one ACS group (n=16).

As with the worst values of ICP, dP and pH, univariate analysis was carried out to determine which factors were associated with the occurrence of ACS. As can be seen from Tables 4.2 and 4.3, none of the demographic or injury related data were associated with an increased risk of developing ACS. Although it appeared initially that the earlier the surgery and monitoring were performed, the more likely the development of ACS, this did not reach statistical significance (Table 4.3).

TABLE 4.2

Chi-squared tests for categorical patient and injury related factors associated with the development of ACS

|  | Gender | RTA | Falls | Work | sport | Tibial fract | Side | Open | Grade |
|---|---|---|---|---|---|---|---|---|---|
| Pchi |  | 0.069 | 0.277 |  |  |  | 0.741 |  | 0.098 |
| Fishers | 0.259 |  |  | 0.686 | 0.686 | 1.000 |  | 0.728 |  |

P values all two-sided

Values are pearsons chi-squared except for those with small numbers in each category which are Fishers exact tests.

TABLE 4.3

Statistical tests for continuous data related to ACS development

|  | Age | Delay to Sx | Delay to Mx | Op length |
|---|---|---|---|---|
| P | 0.980 | 0.063 | 0.080 | 0.522* |

All represent Mann Whitney tests, except *, which was obtained from t-test

Once more, the worst values of the pH, ICP and dP variables were used for the analysis of the association between these test variables and the development of ACS. The initial values of pH, ICP and delta pressure were also tested to detect any predictive value each had for identifying the subsequent development of an ACS. Table 4.4 shows that both the lowest pH and the highest ICP (both peak and average) recorded were significantly different between the two groups, while the delta pressure difference failed to reach statistical significance. Also of interest was the fact that the initial pH value recorded was also significantly different for the two groups.

TABLE 4.4

ACS group versus "others" for test variables pH, ICP and dP

| Variable | Group | Mean | SD | median | Interquartile range | P |
|---|---|---|---|---|---|---|
| Lowest pH | ACS | 6.06 | 0.19 |  |  | 0.000 |
|  | Others | 6.49 | 0.31 |  |  |  |

TABLE 4.4-continued

ACS group versus "others" for test variables pH, ICP and dP

| Variable | Group | Mean | SD | median | Interquartile range | P |
|---|---|---|---|---|---|---|
| High ICP | ACS |  |  | 57 | 35.25; 69.5 | 0.006 |
|  | Others |  |  | 38 | 29; 50.75 |  |
| Ave ICP | ACS |  |  | 54 | 30.5; 58.75 | 0.041 |
|  | Others |  |  | 32 | 22.75; 40.75 |  |
| Lowest dP | ACS |  |  | 8.5 | 0.75; 29.5 | 0.175 |
|  | Others |  |  | 16.5 | 10; 30.75 |  |
| Ave dP | ACS | 17.4 |  | 17 | 2; 36 | 0.379 |
|  | Others | 23.3 |  | 24 | 14.25; 34 |  |
| Initial pH | ACS | 6.48 | 0.27 |  |  | 0.026 |
|  | Others | 6.68 | 0.29 |  |  |  |
| Initial ICP | ACS |  |  | 27 | 17.25; 41.25 | 0.296 |
|  | Others |  |  | 24 | 18.75; 29.25 |  |
| Initial dP | ACS |  |  | 29 | 13; 50.75 | 0.693 |
|  | Others |  |  | 32 | 22.75; 48.75 |  |

Means and standard deviations are displayed for normally distributed variables and medians and interquartile ranges are noted for variables which are not normally distributed.

Having found that the initial pH recorded was predictive of the future development of ACS, the group of IM nails were assessed as to the relationship between the pH, ICP and dP values recorded at each event during surgery and the subsequent occurrence of ACS. Although insufficient numbers existed to test the pre- and post-anaesthetic values (n=9), the pH values recorded at each subsequent event were significantly different for each group. Of the pressure variables, only the post-operative delta pressure was significantly different between the two groups (see table 4.5).

TABLE 4.5

ACS vs normal: Parameters monitored during events of IM nailing with p values (mann whitney)

| | PH | | | ICP (mmHg) | | | Delta Pressure (mmHg) | | |
|---|---|---|---|---|---|---|---|---|---|
| | ACS | Non | p | ACS | non | p | ACS | non | P |
| T | 6.5 | 6.7 | 0.051 | 29 | 24 | 0.338 | 28 | 28 | 0.560 |
| GW | 6.5 | 6.6 | 0.052 | 56.5 | 45 | 0.231 | 1 | 14.5 | 0.377 |
| R | 6.35 | 6.6 | 0.023* | 67 | 48 | 0.224 | −10 | 9.5 | 0.203 |
| N | 6.35 | 6.6 | 0.006** | 77.5 | 59 | 0.108 | −11.5 | 4 | 0.340 |
| TR | 6.3 | 6.8 | 0.003** | 45.5 | 25.5 | 0.185 | 34 | 28 | 0.762 |
| REC | 6.3 | 6.7 | 0.001** | 33 | 26.5 | 0.560 | 27.5 | 46 | 0.023* |

*significant to the 0.05 level (two-tailed)
**significant to the 0.01 level (two-tailed)

Figure 16:
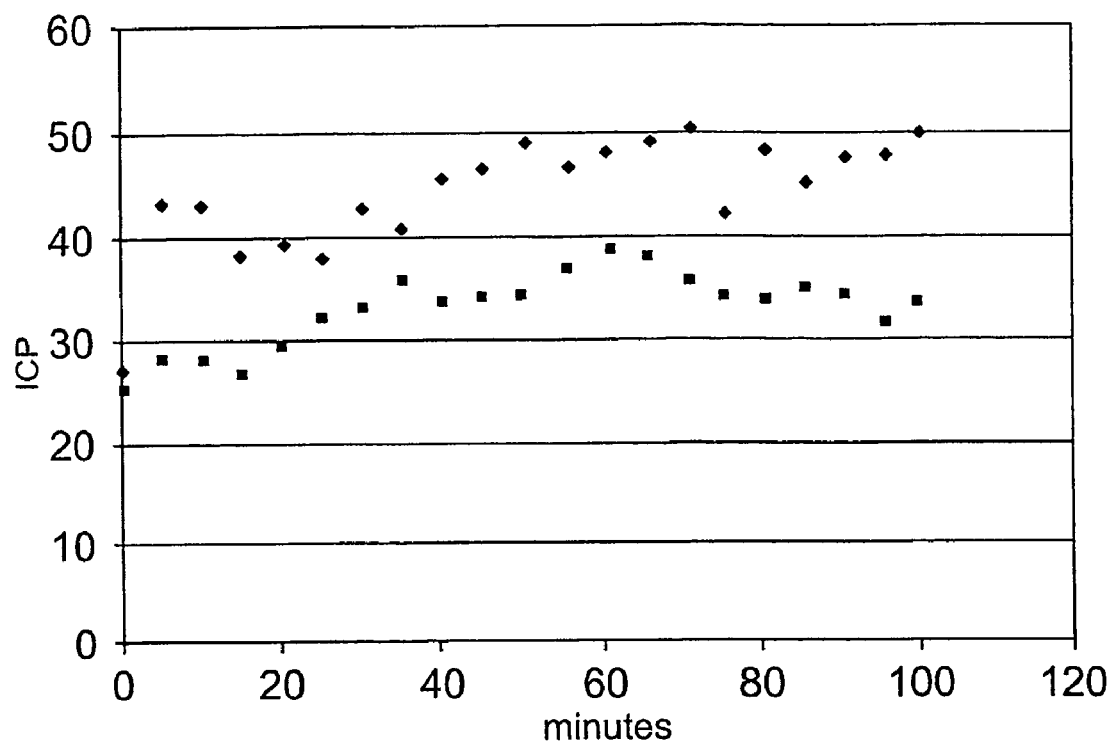
FIG. 16 shows a graph of ICP against time for the patients of example 4 undergoing intramedullary nailing, showing results for patients with ACS and for those without ACS.
Figure 17:
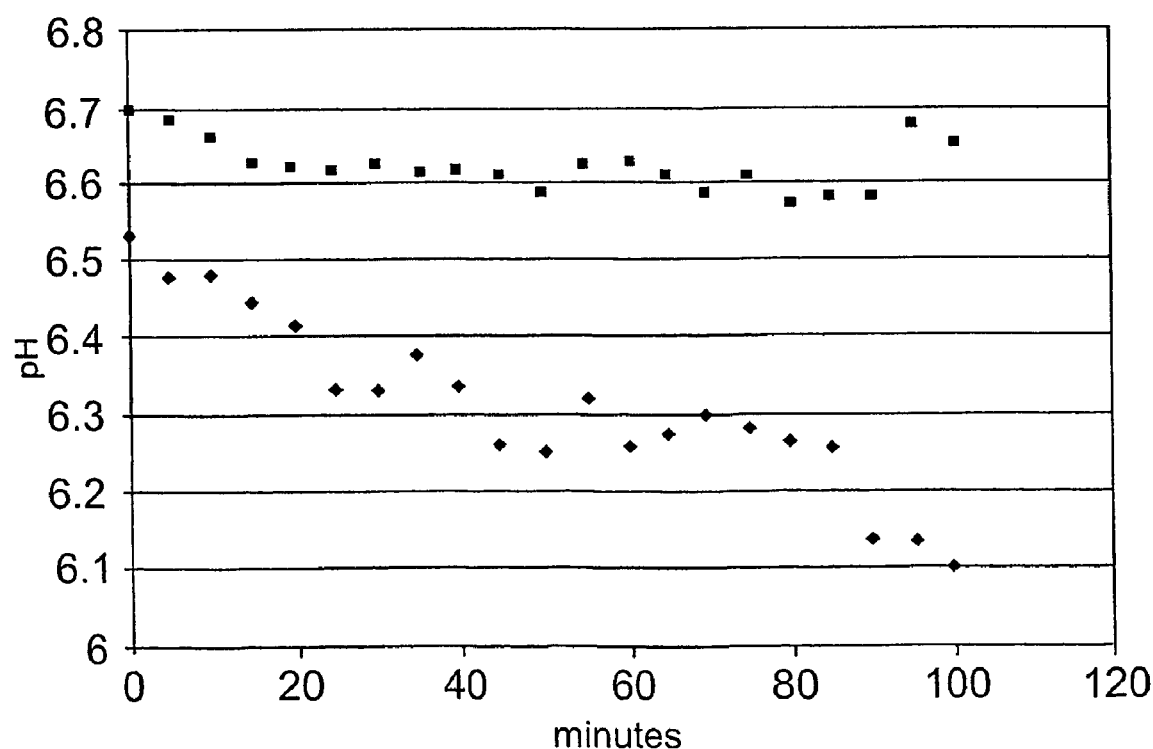
FIG. 17 shows a graph of pH against time for the patients of example 4 undergoing intramedullary nailing, for patients with ACS and for those without ACS.

FIGS. 16 and 17 are graphs of absolute ICP and pH respectively during Intramedullary nailing. The diamonds represent the ACS group and the squares represent the ACS group.

Recovery Following Fasciotomies

Figure 18:
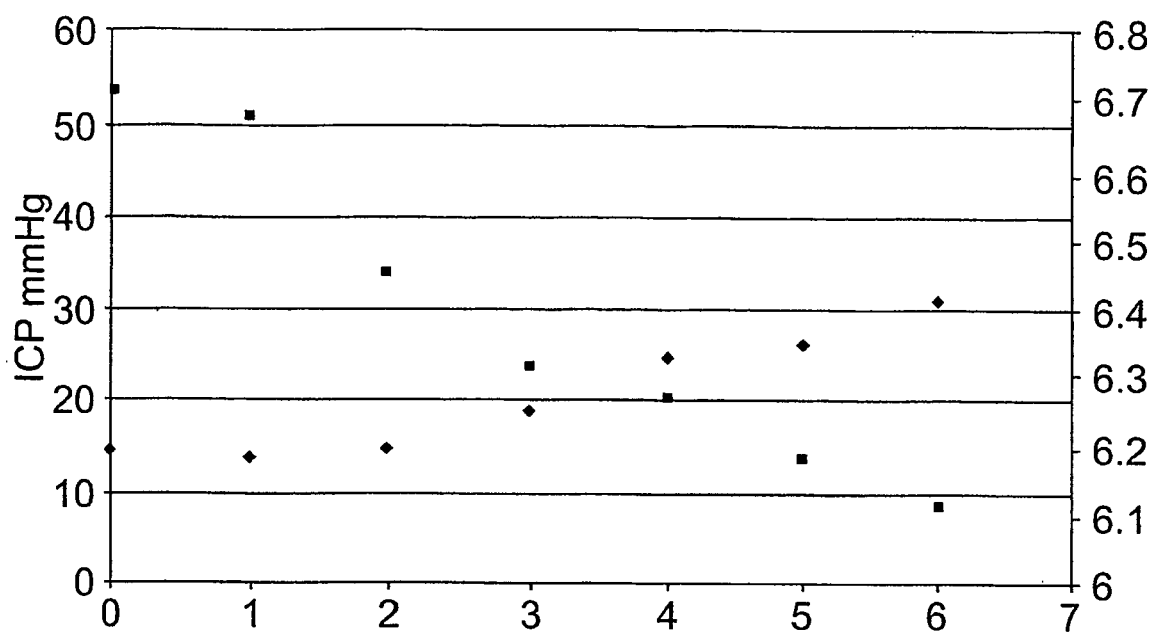
FIG. 18 shows a graph of ICP and pH against the time of certain events of fasciotomies for patients of example 4.

Twelve patients underwent fasciotomies during this study. Data was collected throughout the procedure, and each variable was recorded at specific time points: Prior to fasciotomies, and following each dermotomy, and each fasciotomy. The data obtained is displayed in FIG. 18. The diamonds represent pH and the squares represent pressure. Both pH and pressure recovered during the surgery, however, although the pressure had significantly reduced following the last fasciotomy (p=0.008), the pH had not recovered significantly by this time point (p=0.284).

Intra-Compartmental Pressure vs pH

Figure 19:
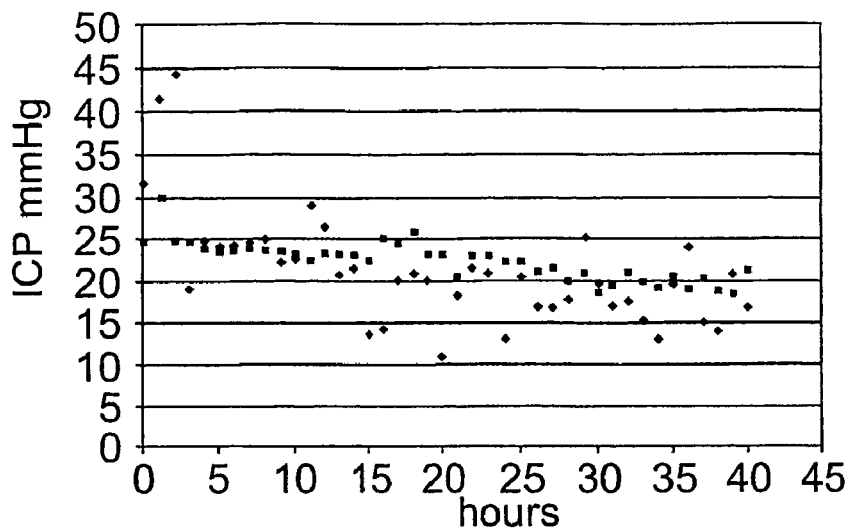
FIG. 19 shows a graph of ICP against time for the full group of patients in example 4, showing results for both patients with ACS (diamonds) and without ACS (squares)
Figure 20:
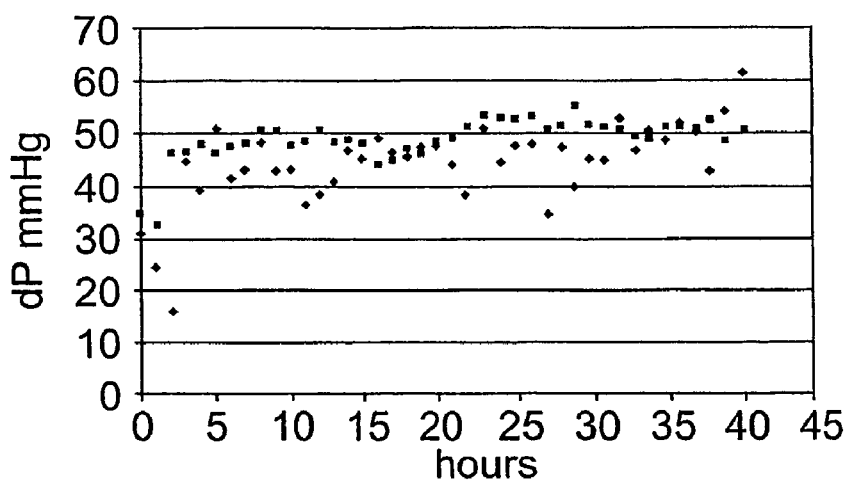
FIG. 20 shows a graph of delta pressure against time for the full group of patients in example 4, showing results for both patients with ACS (diamonds) and without ACS (squares)
Figure 21:
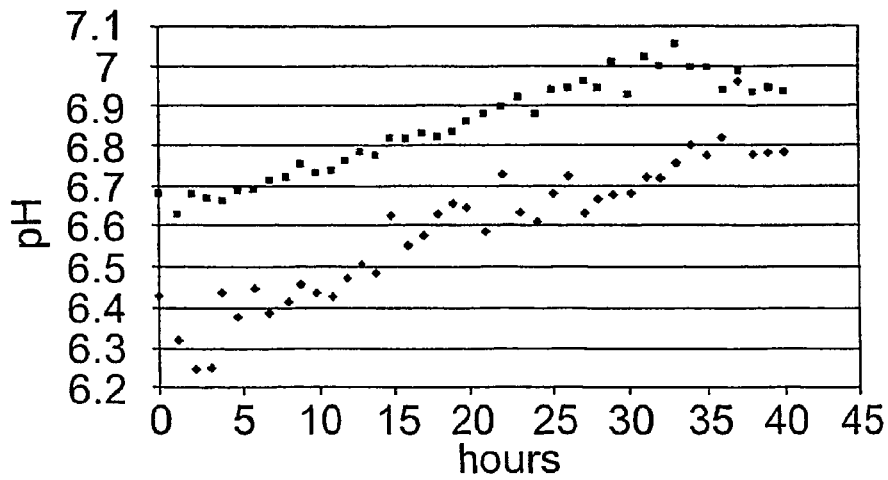
FIG. 21 shows a graph of pH against time for the full group of patients in example 4, showing results for both patients with ACS (diamonds) and without ACS (squares)

In order to further compare the diagnostic strength of pressure based variables with pH in relation to ACS, the initial full group graphs were split into those with, and those without signs of ACS. In addition, the sensitivity and specificity for each level of each variable was calculated, and ROC curves produced. Finally, further univariate analysis was carried out using the best levels of each variable identified via the previous tests. The data for ICP, delta pressure and pH over the first 40 hours following injury are presented in FIGS. 19 to 21 respectively. For pressure related data, the only values which were significantly different between the groups occurred at the 1 and 2 hour points for ICP (p=0.043; p=0.000), and only at the 2 hour point for dP (p=0.000). However, the pH values recorded for the ACS group were significantly different from those without the syndrome for each time point up to 33 hours. This shows that pH readings can provide a better indication of acute compartment syndrome than ICP readings. Furthermore, the slope of the line is similar in the recovery period.

Correlations were performed comparing the three variables being tested to determine any relationship that existed between pH and pressure based recordings; the results are shown in Table 4.6. As expected, the ICP and dP values were highly correlated (dP=diastolic blood pressure—ICP), and the initial pH values correlated well with the lowest pH values subsequently recorded. However, neither the lowest pH nor the initial pH values obtained were correlated with either pressure measurement.

TABLE 4.6

Correlations between ICP, dP, and pH values recorded

|  | Low pH | High ICP | Low dP | Initial pH | Initial ICP | Initial dP |
|---|---|---|---|---|---|---|
| Low pH |  | 0.560 | 0.549 | 0.000* | 0.830 | 0.495 |
| High ICP | 0.560 |  | 0.000* | 0.489 | 0.000* | 0.005* |
| Low dP | 0.549 | 0.000* |  | 0.153 | 0.000* | 0.000* |
| Initial pH | 0.000* | 0.489 | 0.153 |  | 0.714 | 0.196 |
| Initial ICP | 0.830 | 0.000* | 0.000* | 0.714 |  | 0.000* |
| Initial dP | 0.495 | 0.005* | 0.000* | 0.196 | 0.000* |  |

All correlations are Spearman's rho, except those comparing pH values (Pearson's correlations)
*correlation significant to the 0.01 level (two-tailed)

Figure 22:
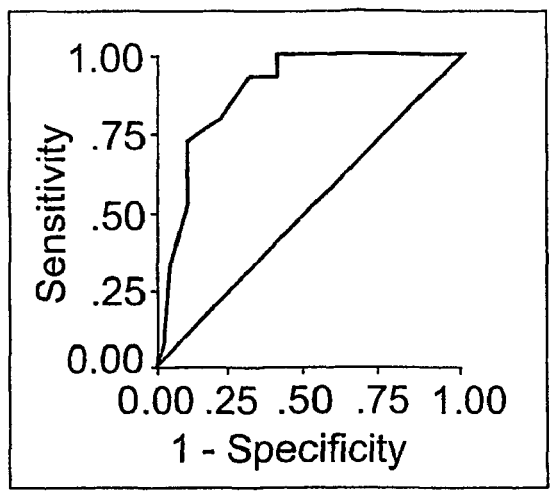
FIG. 22 shows a ROC curve for pH for the patients of example 4.
Figure 23:
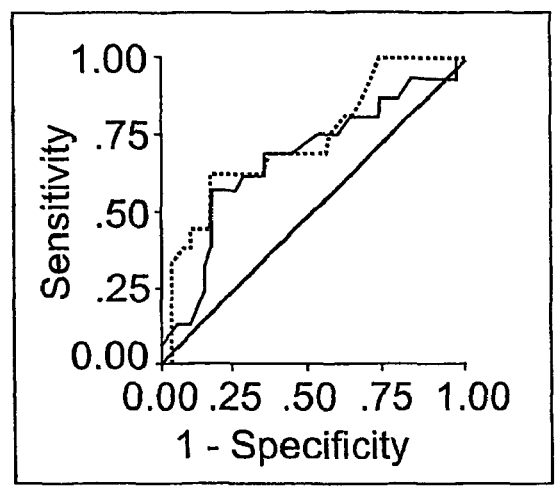
FIG. 23 shows a ROC curve for ICP for the patients of example 4.
Figure 24:
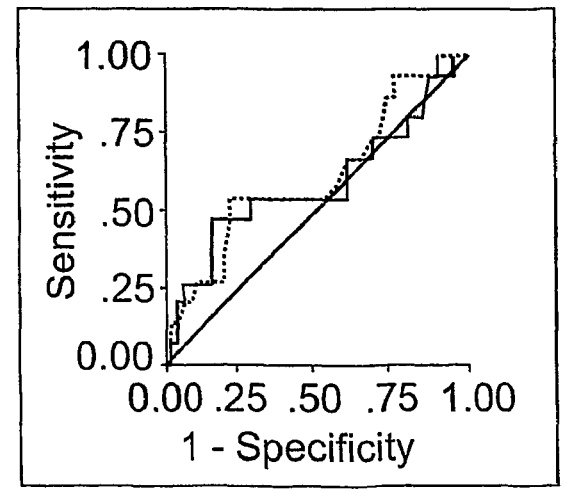
FIG. 24 shows a ROC curve for delta pressure for the patients of example 4.

The sensitivity and specificity for pH, ICP and delta pressure were calculated, allowing ROC curves to be produced (FIGS. 22 to 24 respectively).

Area under curves:

| lowest pH: | 0.875 |
|---|---|
| Highest ICP: | 0.732 |
| average high ICP: | 0.673 |
| Lowest dP: | 0.591 |
| average low dP: | 0.577 |

Figure 25:
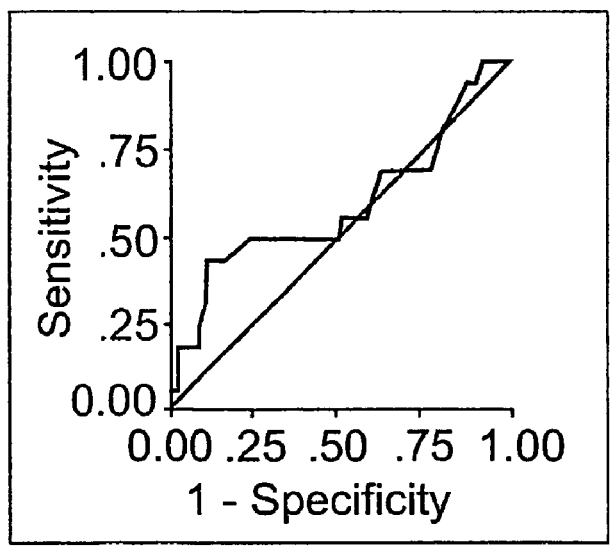
FIG. 25 shows a ROC curve for initial ICP for the patients of example 4.
Figure 26:
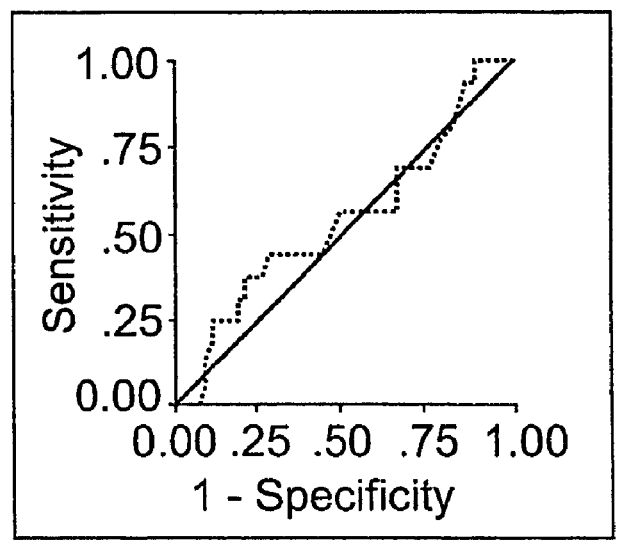
FIG. 26 shows a ROC curve for initial delta pressure for the patients of example 4.
Figure 27:
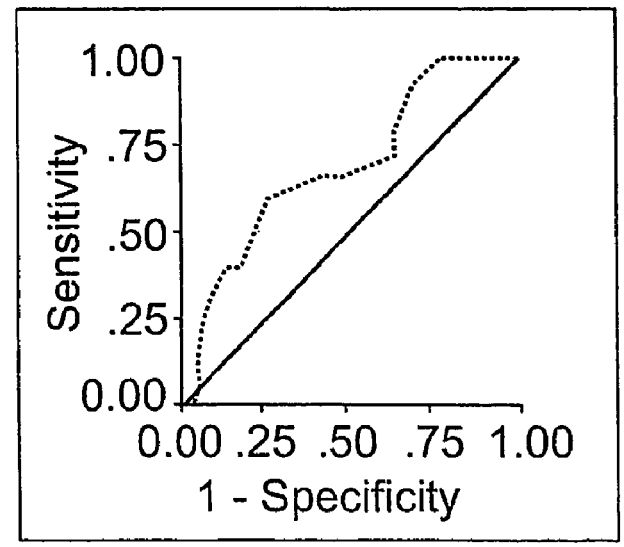
FIG. 27 shows a ROC curve for initial pH for the patients of example 4.

Given the significance of the initial pH value at predicting ACS, the sensitivity and specificity were also calculated for initial ICP, initial delta pressure and initial pH, and the results are displayed in FIGS. 25 to 27 respectively.

Areas under curve:

| ICP: | 0.589 |
|---|---|
| DP: | 0.540 |
| PH: | 0.681 |

By examining the sensitivity and specificity for each variable from the ROC curves generated, the best levels at which to diagnose ACS for each variable were determined. This was less than 6.4 for pH (93% sensitivity, 68% specificity), greater than 40 mmHg for ICP (69% sensitivity, 66% specificity) and less than 20 mmHg for delta pressure (53% sensitivity, 64% specificity). Chi-squared tests were then used for each variable, and only the critical pH and ICP levels identified were associated with development of the syndrome (table 4.7). Chi squared tests were also carried out on the most commonly used pressure-based criteria for ACS currently (table 4.8).

TABLE 4.7

Chi-squared tests for best fit predictive measurements associated with the development of ACS (pearsons chi)

|  | pH < 6.4 | ICP > 40 | DP < 20 |
|---|---|---|---|
| Pchi | 0.000 | 0.039 | 0.167 |

TABLE 4.9

Chi-squared tests for predictive value of currently used levels of ICP and dP

|  | ICP > 30 | ICP > 40 | ICP > 50 | DP < 30 |
|---|---|---|---|---|
| Pchi | 0.195 | 0.039 | 0.002 | 0.481* |

Values are pearsons chi, except * fishers exact test

RESULTS FOR EXAMPLE 5 pH

The first point of attack of ischaemia is the cell's aerobic respiration, i.e. oxidative phosphorylation by the mitochondria. As the oxygen tension within the cell decreases there is a loss of oxidative phosphorylation and decreased generation of ATP.

This switch to anaerobic metabolism results in an increased rate of glycolysis designed to maintain the cells energy sources by generating ATP through the metabolism of glucose derived from glycogen. As a consequence glycogen stores are rapidly depleted, resulting in the accumulation of lactic acid and inorganic phosphates from the hydrolysis of phosphate esters. This reduces the intracellular and interstitial pH.

Table 5.1 displays the decrease in muscle pH in relation to ischaemic time.

TABLE 5.1 displays the decrease in muscle pH in relation to ischaemic time.

| Time (min) | pH | SD |
|---|---|---|
| 0 | 7.14 | 0.05 |
| 2 | 6.95 | 0.05 |
| 4 | 6.84 | 0.07 |
| 6 | 6.76 | 0.09 |
| 8 | 6.70 | 0.10 |
| 10 | 6.65 | 0.11 |
| 15 | 6.57 | 0.11 |
| 30 | 6.44 | 0.08 |
| 45 | 6.35 | 0.07 |
| 60 | 6.31 | 0.08 |
| 75 | 6.29 | 0.09 |
| 90 | 6.26 | 0.07 |
| 105 | 6.24 | 0.05 |
| 120 | 6.22 | 0.04 |
| 135 | 6.21 | 0.04 |
| 150 | 6.18 | 0.04 |

Figure 28:
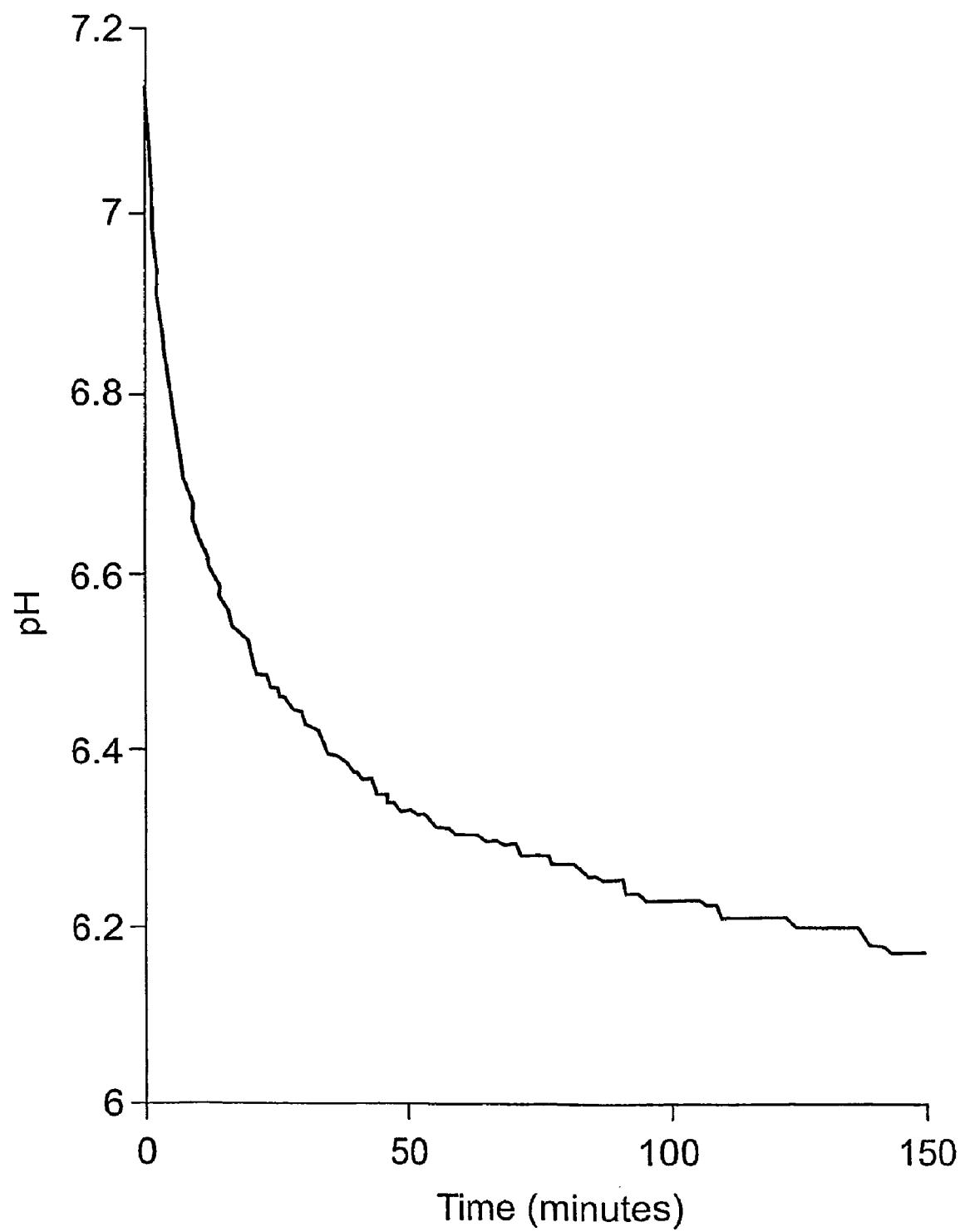
FIG. 28 shows a graph of pH decline over time during muscle ischaemia.

Although tissue oxygen levels are depleted rapidly after the onset of muscle ischaemia, tissue pH continues to decline over a prolonged period under similar conditions. This is clearly visible in FIG. 28.

Glucose 6 Phosphate

Glucose 6 phosphate (G6P) acts as a key crossroads governing the metabolism. Glucose entering the cell can rapidly be phosphorylated to G6P, which can be stored as glycogen, degraded by way of pyruvate, or converted into ribose 5 phosphate.

Under "normal conditions", G6P can be formed by the mobilization of glycogen, or it can be synthesised from pyruvate or glycogenic amino acids by the gluconeogenic pathway. However during ischaemia and anaerobic metabolism, Glucose 6 phosphate acts as a crossroads feeding the glucose molecules into the glycolytic pathway, in an attempt to maintain ATP levels.

TABLE 5.2

| pH | [G6P] | SD |
|---|---|---|
| 7.1 | 1.89 | 0.29 |
| 7 | 1.77 | 0.24 |
| 6.9 | 1.45 | 0.39 |
| 6.8 | 1.36 | 0.35 |
| 6.7 | 0.78 | 0.12 |
| 6.6 | 0.76 | 0.09 |
| 6.5 | 0.57 | 0.07 |
| 6.4 | 0.52 | 0.06 |
| 6.3 | 0.48 | 0.12 |
| 6.2 | 0.39 | 0.04 |

Figure 29:
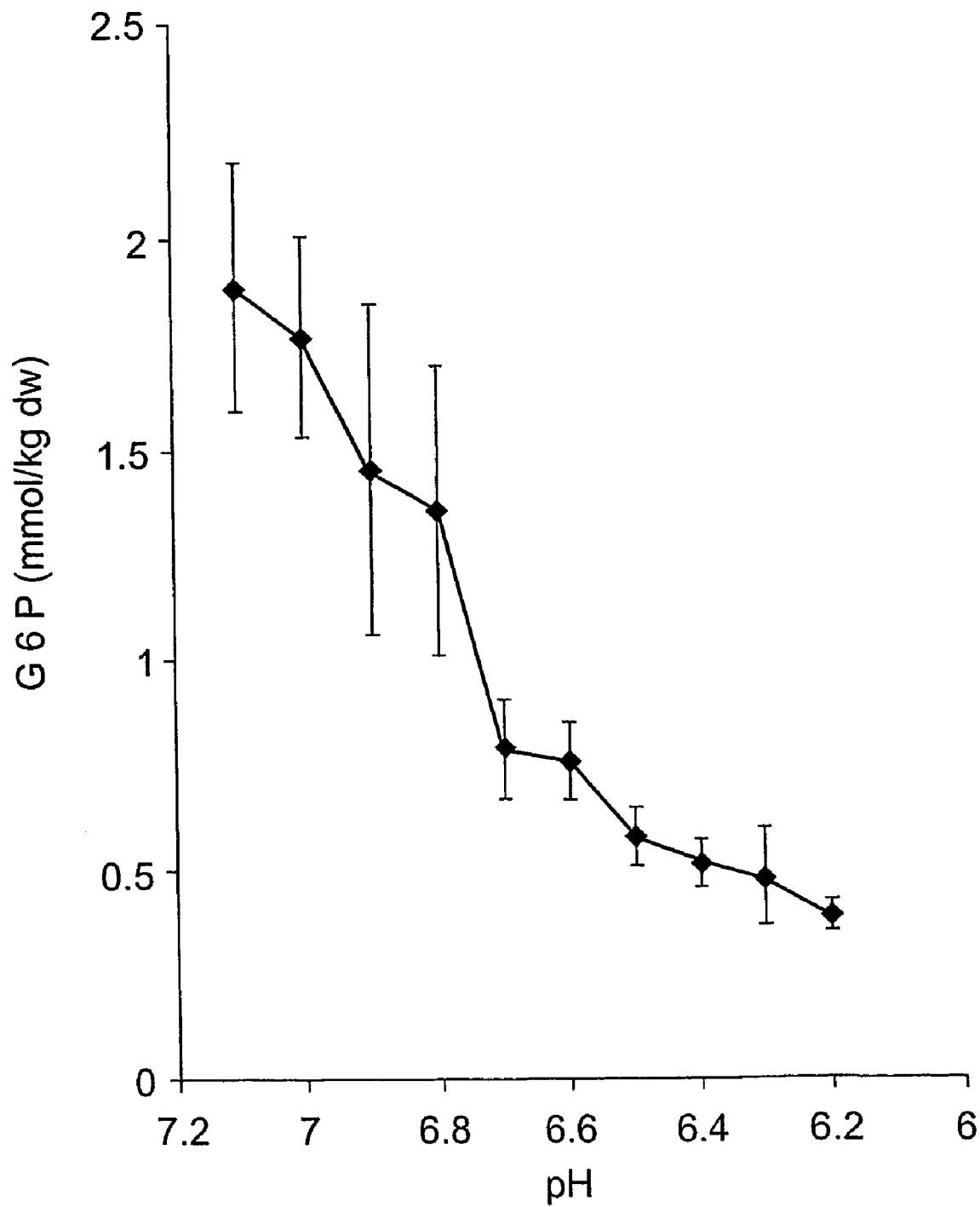
FIG. 29 shows a graph of G6P decline over time during muscle ischaemia.

Both Table 5.2 and FIG. 29 clearly demonstrate the rapid fall of G6P with the onset and progression of ischaemia.

Lactate

Under anaerobic conditions, the reduction of pyruvate to lactate consumes NADH and regenerates $NAD^+$ that is essential for continued glycolysis.

The reduction of pyruvate is catalysed by Lactate Dehydrogenase, which forms the L isomer of lactic acid. The overall equilibrium of this reaction strongly favours lactate formation and once formed, lactate can only be reconverted to pyruvate in the liver. Hence, within the muscle, lactate is a metabolic dead end.

TABLE 5.3

| pH | [Lactate] | SD |
|---|---|---|
| 7.1 | 17.67 | 8.50 |
| 7 | 31.00 | 9.93 |
| 6.9 | 46.71 | 7.30 |
| 6.8 | 51.33 | 4.63 |
| 6.7 | 64.80 | 8.93 |
| 6.6 | 82.50 | 11.12 |
| 6.5 | 95.67 | 7.50 |
| 6.4 | 127.00 | 5.00 |
| 6.3 | 140.67 | 15.37 |
| 6.2 | 164.67 | 9.29 |

Figure 30:
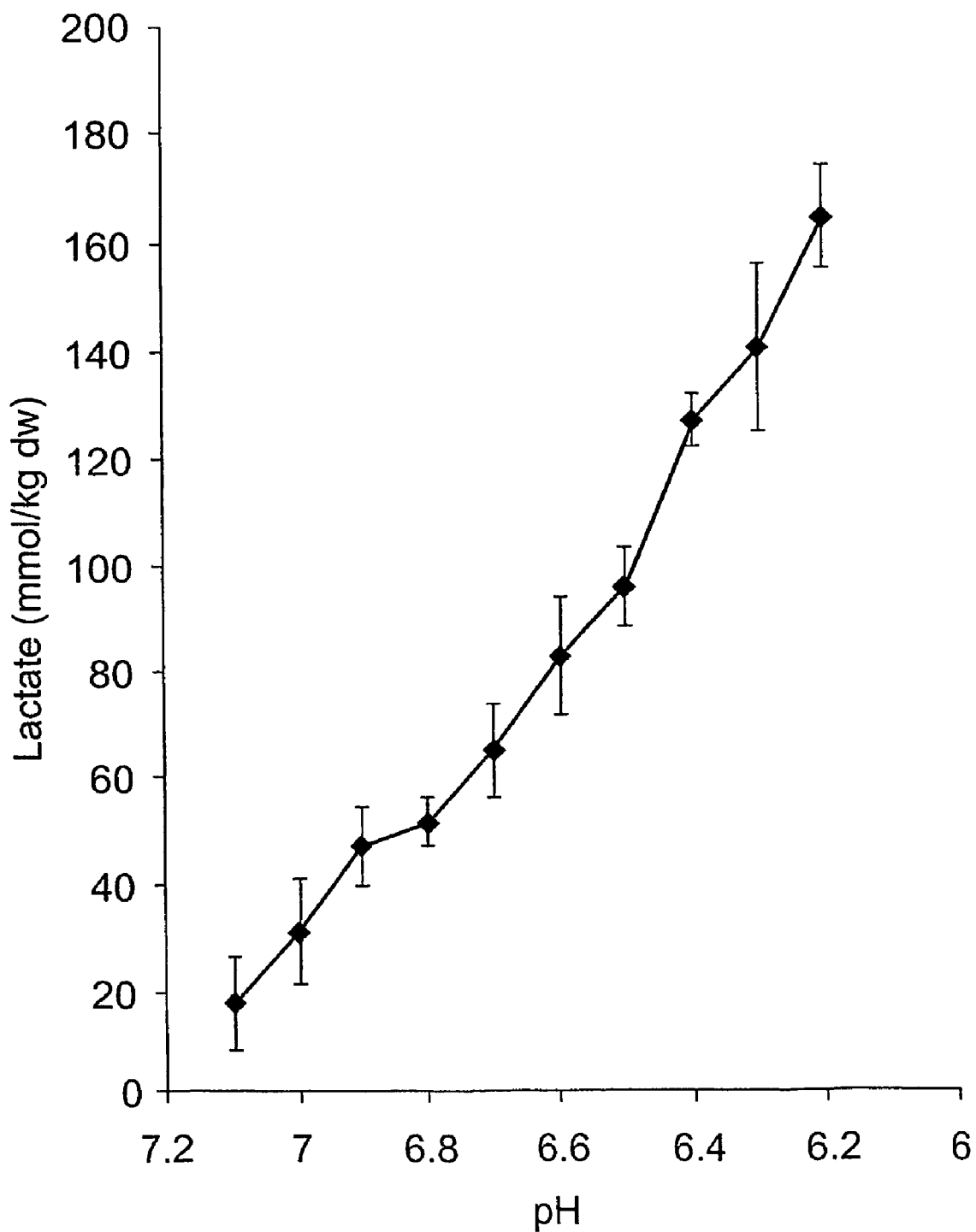
FIG. 30 shows a graph of lactate concentration increase over time during muscle ischaemia.

Both Table 5.3 and FIG. 30 clearly demonstrate the gradual elevation of Lactate within the muscle tissue, with the progression of ischaemia.

We know that the pathophysiology of ACS results in inadequate tissue oxygen delivery, precipitating anaerobic metabolism. However in addition ACS impairs the removal of the products of anaerobic glycolysis, and one might hypothesise that this may result in an increased accumulation of lactic acid.

Pyruvate

Pyruvate, the product of glycolysis, represents an important junction point in carbohydrate metabolism. The initial steps of glycolysis or glycogenolysis are anaerobic and are the predominant metabolic pathways of energy production for preservation of cell integrity in ischaemic skeletal muscle.

The reactions of glycolysis occur in the cytoplasm of the cell, and the pyruvate formed is not phosphorylated and is, therefore, free to leave the cell. Some pyruvate will escape from tissues such as muscle when the rate of glycolysis is high, but most is further metabolised. Pyruvate produced by glycolysis during ischaemia is ultimately metabolised under anaerobic conditions to form lactate.

TABLE 5.4

| pH | [Pyruvate] | SD |
|---|---|---|
| 7.1 | 1.60 | 0.27 |
| 7 | 1.58 | 0.25 |
| 6.9 | 1.50 | 0.41 |
| 6.8 | 1.20 | 0.22 |
| 6.7 | 0.96 | 0.33 |
| 6.6 | 0.62 | 0.20 |
| 6.5 | 0.56 | 0.22 |
| 6.4 | 0.46 | 0.21 |
| 6.3 | 0.46 | 0.17 |
| 6.2 | 0.26 | 0.09 |

Figure 31:
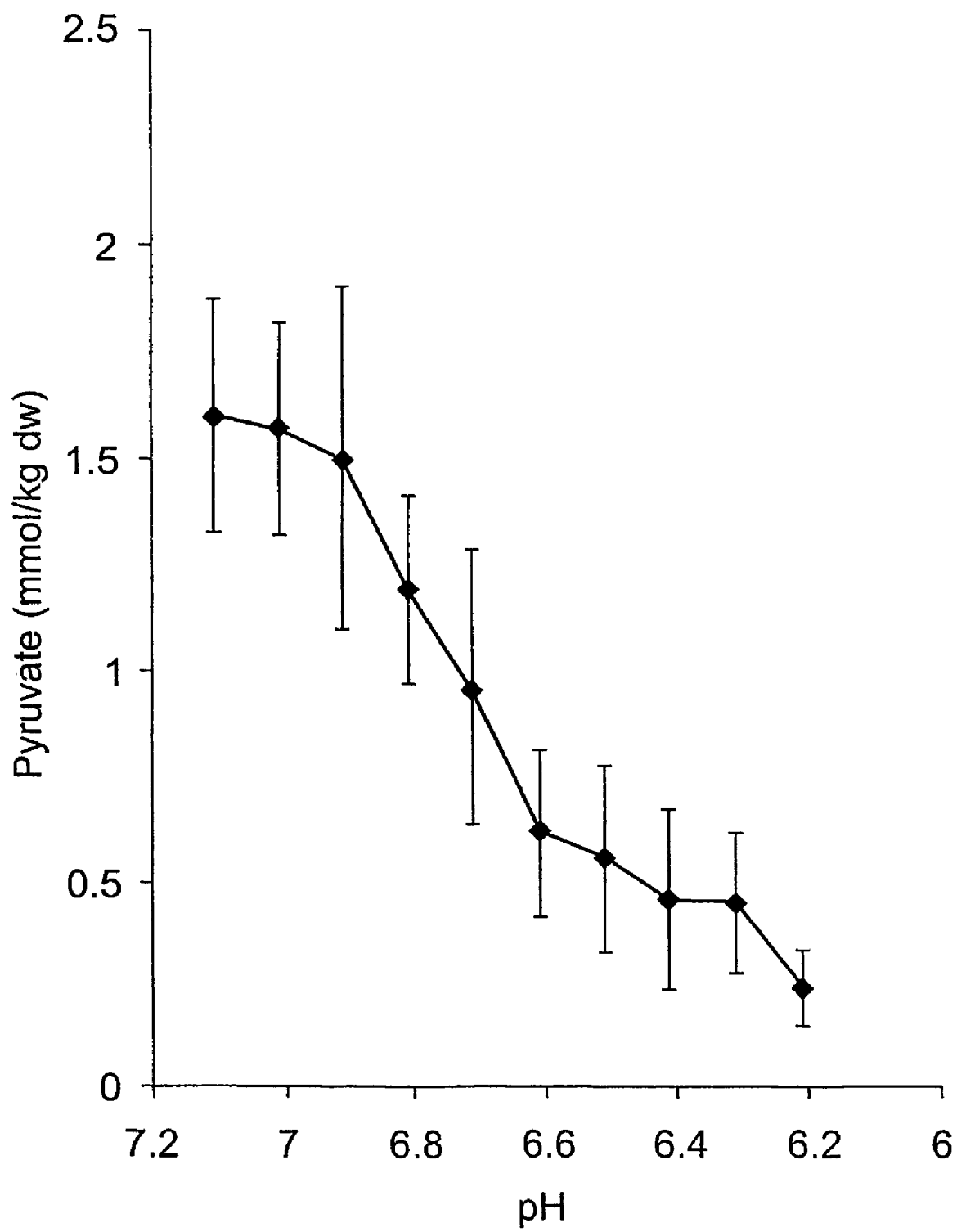
FIG. 31 shows a graph of pyruvate concentration decline over time during muscle ischaemia.

Table 5.4 and FIG. 31 demonstrate the fall of tissue Pyruvate concentrations. These closely mirror the similar fall in G6P concentrations, which support the gradual utilisation of the glycolyic metabolites with ensuing ischaemia.

pH Verification

Previous studies performed by Sahlin et al found a close relationship between pH and the concentrations of lactate and pyruvate in skeletal muscle at rest and following various levels of circulatory occlusion.

$$pH=-0.00532(lactate+pyruvate)+7.06$$

This enables us to verify the pH measurements of the intramuscular probe with a calculated pH, derived from the above assay results.

The Intramuscular pH measurements and corresponding lactate concentration, pyruvate concentration and calculated pH are demonstrated in table 5.5.

TABLE 5.5

| Specimen No | IM pH measurement | [Lactate] mmol/kg | [Pyruvate] mmol/kg | Calc. pH measurement |
|---|---|---|---|---|
| 1.00 | 6.90 | 46.00 | 1.73 | 6.81 |
| 2.00 | 6.80 | 51.00 | 0.86 | 6.78 |
| 3.00 | 6.70 | 55.00 | 1.69 | 6.76 |
| 4.00 | 6.90 | 49.00 | 1.79 | 6.79 |
| 5.00 | 6.80 | 55.00 | 1.49 | 6.76 |
| 6.00 | 6.70 | 60.00 | 1.17 | 6.73 |
| 7.00 | 6.50 | 98.00 | 0.91 | 6.53 |
| 8.00 | 6.90 | 43.00 | 0.69 | 6.83 |
| 9.00 | 6.70 | 59.00 | 0.52 | 6.74 |
| 10.00 | 6.70 | 76.00 | 0.67 | 6.65 |
| 11.00 | 6.60 | 86.00 | 0.46 | 6.60 |
| 12.00 | 6.80 | 45.00 | 1.14 | 6.81 |
| 13.00 | 6.70 | 55.00 | 0.84 | 6.76 |
| 14.00 | 6.60 | 70.00 | 0.49 | 6.68 |
| 15.00 | 6.50 | 85.00 | 0.37 | 6.61 |
| 16.00 | 6.90 | 44.00 | 1.75 | 6.82 |
| 17.00 | 6.80 | 57.00 | 1.39 | 6.75 |
| 18.00 | 6.70 | 58.00 | 1.16 | 6.75 |
| 19.00 | 6.70 | 64.00 | 0.85 | 6.71 |
| 20.00 | 6.60 | 78.00 | 0.62 | 6.64 |
| 21.00 | 6.90 | 43.00 | 1.49 | 6.82 |
| 22.00 | 7.00 | 31.00 | 1.89 | 6.89 |
| 23.00 | 6.50 | 90.00 | 0.35 | 6.58 |
| 24.00 | 6.20 | 175.00 | 0.21 | 6.13 |
| 26.00 | 7.10 | 26.00 | 1.90 | 6.91 |
| 27.00 | 6.90 | 40.00 | 1.79 | 6.84 |
| 28.00 | 6.60 | 96.00 | 0.90 | 6.54 |
| 29.00 | 6.40 | 132.00 | 0.69 | 6.35 |
| 30.00 | 6.30 | 148.00 | 0.59 | 6.27 |
| 31.00 | 6.30 | 151.00 | 0.51 | 6.25 |
| 32.00 | 6.20 | 162.00 | 0.36 | 6.20 |
| 33.00 | 7.00 | 45.00 | 1.66 | 6.81 |
| 34.00 | 6.90 | 62.00 | 1.28 | 6.72 |
| 35.00 | 6.70 | 79.00 | 0.74 | 6.64 |
| 36.00 | 6.50 | 94.00 | 0.70 | 6.56 |
| 37.00 | 6.30 | 123.00 | 0.27 | 6.40 |
| 38.00 | 6.20 | 157.00 | 0.20 | 6.22 |
| 39.00 | 7.10 | 9.00 | 1.36 | 7.00 |
| 40.00 | 7.00 | 23.00 | 1.38 | 6.93 |
| 41.00 | 6.80 | 47.00 | 1.11 | 6.80 |
| 42.00 | 6.70 | 68.00 | 0.99 | 6.69 |
| 43.00 | 6.50 | 105.00 | 0.60 | 6.50 |
| 44.00 | 6.40 | 122.00 | 0.43 | 6.41 |
| 45.00 | 7.10 | 18.00 | 1.55 | 6.96 |
| 46.00 | 7.00 | 25.00 | 1.37 | 6.92 |
| 47.00 | 6.80 | 53.00 | 1.19 | 6.77 |
| 48.00 | 6.70 | 74.00 | 0.98 | 6.66 |
| 49.00 | 6.50 | 102.00 | 0.41 | 6.52 |
| 50.00 | 6.40 | 127.00 | 0.27 | 6.38 |

Figure 32:
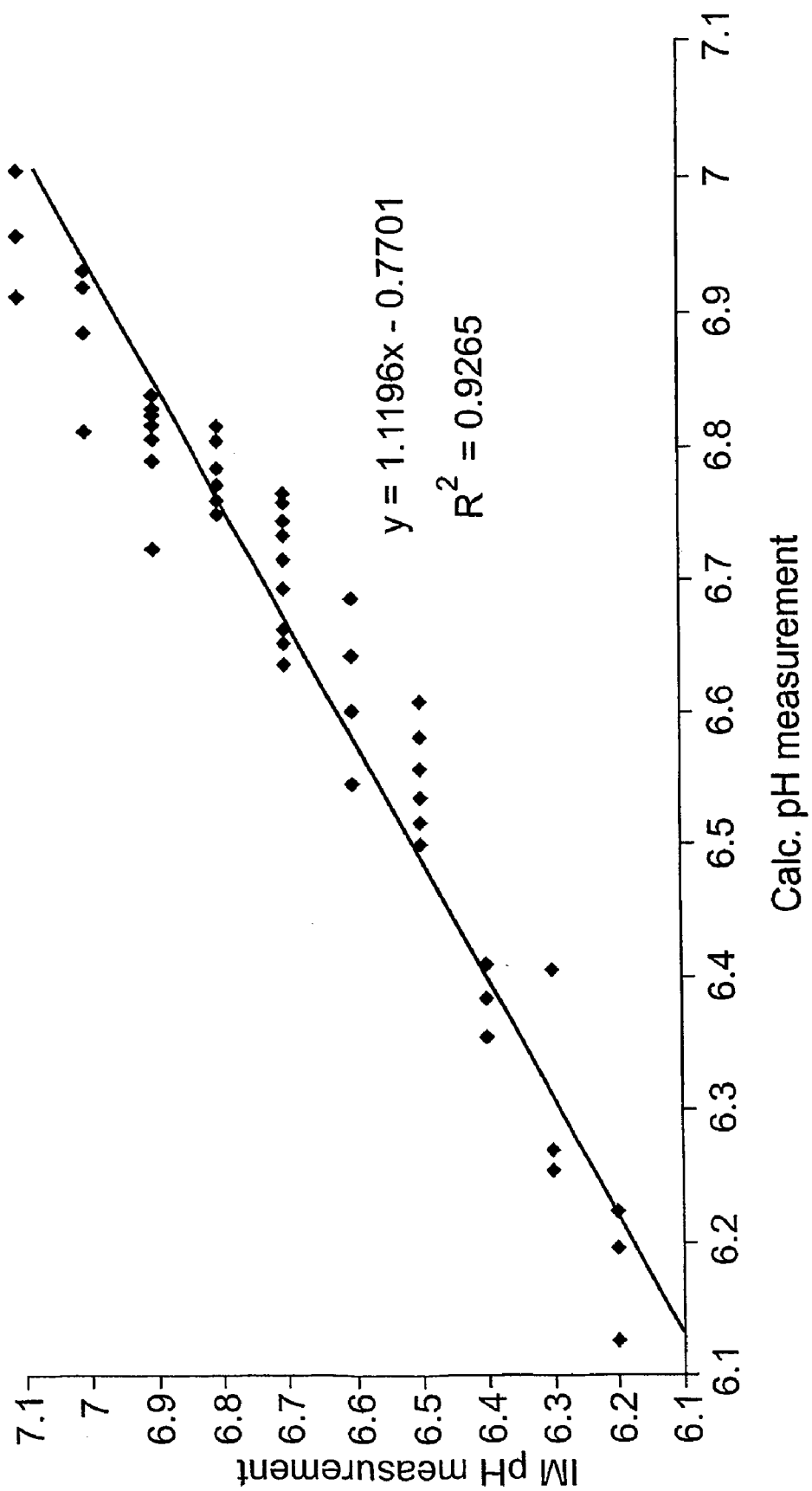
FIG. 32 shows a plot of intramuscular (measured) pH values against calculated pH values.

A simple plot of the results of Intramuscular vs. Calculated pH (FIG. 32) demonstrate the results lying near the line of equality, the line on which all points would lie if the two measurements were exactly the same, every time. The Trend line of these points gave an equation $y=1.1196x-0.7701$ with an $R^2=0.9265$. The high correlation of the results shows that the pH probe is providing consistent and reliable results.

Figure 33:
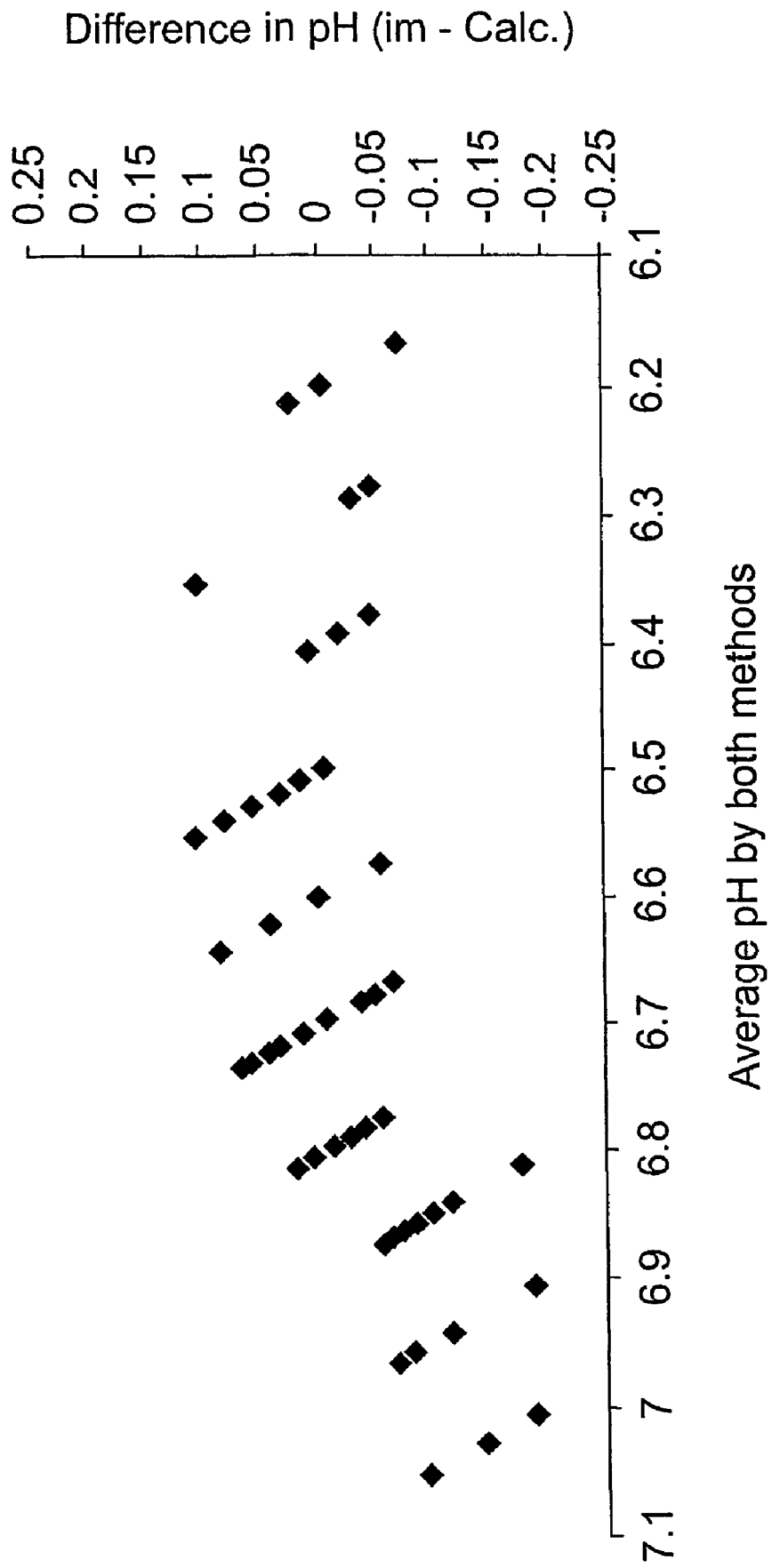
FIG. 33 shows a measurement of agreement curve of the FIG. 32 data.

To assess where any bias lies between the Intramuscular and Calculated pH measurements, a Measurement of Agreement curve was constructed (FIG. 33), comparing the average of the corresponding pHs to the difference between the corresponding pHs. This demonstrated the greatest bias lies at the upper pH levels of 7.1 to 6.8, which actually corresponds to the physiological range of muscle ischaemia.

ATP and PCr

Within the cells, reactions which are not thermodynamically favoured may nevertheless be driven if coupled to reactions that have large, negative free energy changes. In living systems, the hydrolysis of certain phosphate compounds is frequently used in such coupling. The phosphate transfer potential ranks these compounds according to their ability to phosphorylate other compounds under standard conditions. Adenosine Triphosphate (ATP) lies about midway on the scale of phosphate transfer potential. This position is a strategic one, for ATP serves as the general "free energy currency" for virtually all cellular processes and is essential for the maintenance cell function and integrity.

There are several metabolites with greater phosphate transfer potentials than ATP. Phosphocreatine, otherwise known as creatine phosphate, is such a compound. It is abundant in skeletal muscle, with quantities 4 times that of ATP. There it acts as a shuttle and a reservoir of the phosphate bond energy from the ATP in the mitochondria to the myofibrils, where its energy is transduced to the mechanical energy of muscle contraction.

Figure 34:
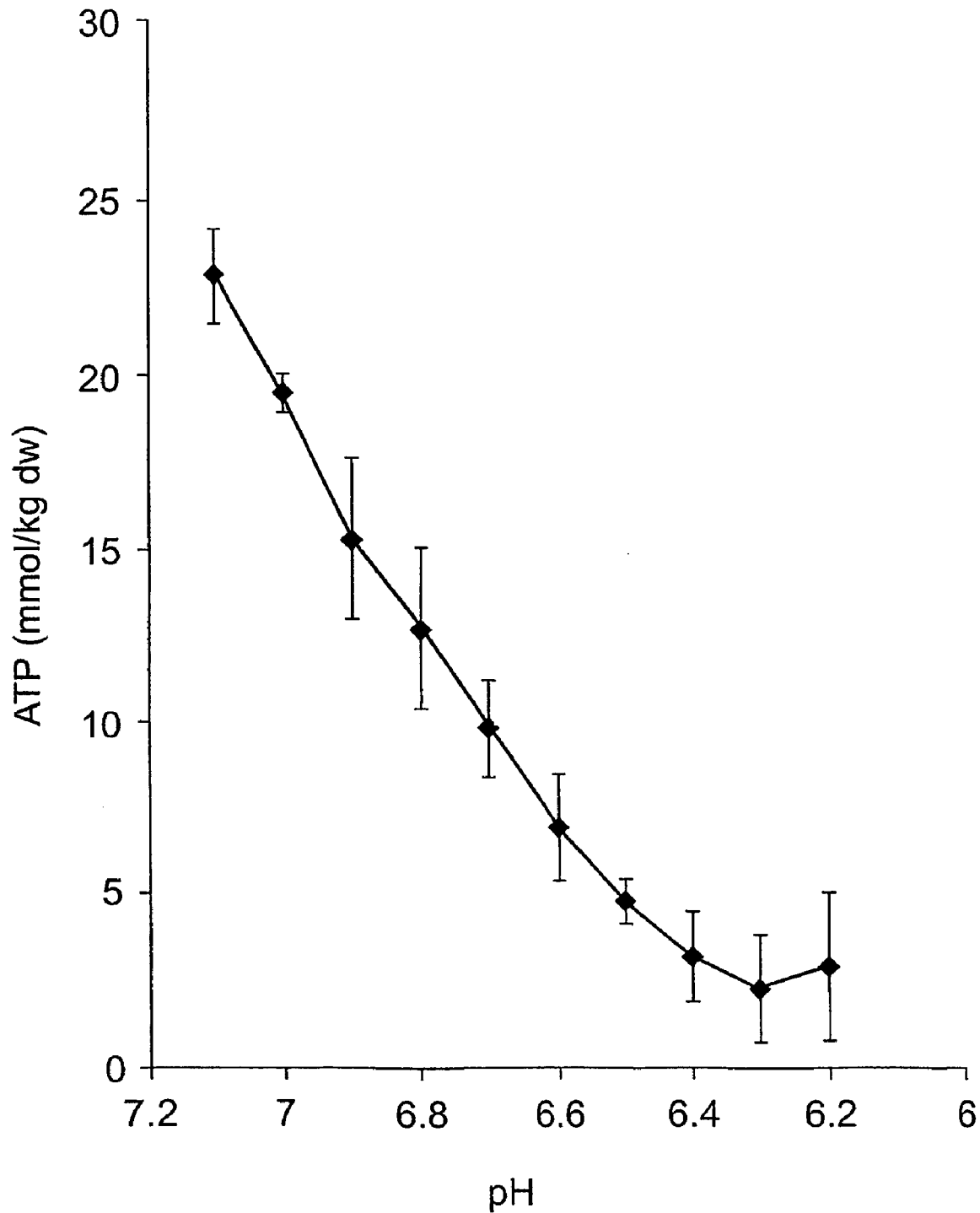
FIGS. 34, 35 show graphs of the decline in ATP and PCr respectively over time during muscle ischaemia.
Figure 35:
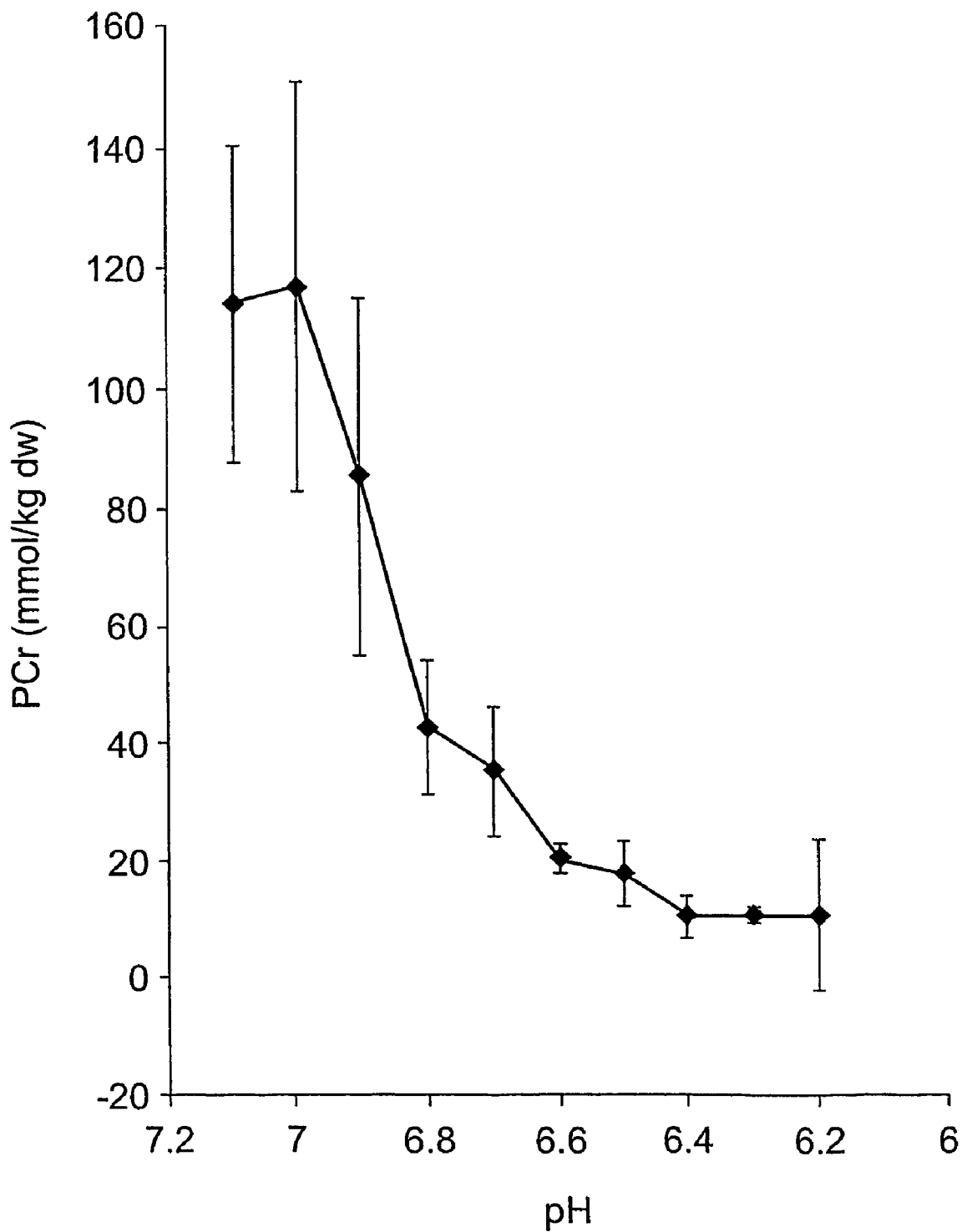

Tables 5.6 and 5.7 display the fall of both ATP and PCr with decreasing pH. These are further demonstrated on FIGS. 34 and 35.

TABLE 5.6

| pH | [ATP] | SD |
|---|---|---|
| 7.10 | 22.82 | 1.35 |
| 7.00 | 19.52 | 0.53 |
| 6.90 | 15.31 | 2.36 |
| 6.80 | 12.73 | 2.38 |
| 6.70 | 9.81 | 1.40 |
| 6.60 | 6.96 | 1.56 |
| 6.50 | 4.83 | 0.64 |
| 6.40 | 3.23 | 1.31 |
| 6.30 | 2.32 | 1.54 |
| 6.20 | 2.99 | 2.12 |

TABLE 5.7

| pH | [PCr] | SD |
|---|---|---|
| 7.10 | 114.03 | 26.53 |
| 7.00 | 117.09 | 33.94 |
| 6.90 | 85.40 | 30.07 |
| 6.80 | 42.82 | 11.46 |
| 6.70 | 35.59 | 11.12 |
| 6.60 | 20.63 | 2.47 |
| 6.50 | 18.12 | 5.57 |
| 6.40 | 10.89 | 3.55 |
| 6.30 | 11.29 | 0.87 |
| 6.20 | 11.40 | 12.68 |

As ischaemia commences, the oxygen tension within the cell decreases and there is a loss of oxidative phosphorylation and decreased generation of ATP. At this point, the metabolic demand of the cell can no longer be met via aerobic metabolism and anaerobic processes begin in earnest. The switch to anaerobic metabolism results in an increased rate of glycolysis designed to maintain the cell's energy sources by generating ATP through the metabolism of glucose derived from glycogen. However with increased duration of ischaemia these reserves are utilised with resulting depletion of ATP. This depletion of ATP has widespread effects on many systems of the cell. If ischaemia persists, irreversible injury ensues and ischaemic tissue death ultimately occurs. This process has morphological hallmarks, but the biochemical explanation for the critical transition from the reversible injury to cell death has remained elusive.

However, two phenomena consistently characterise irreversibility. The first is the inability to reverse mitochondrial dysfunction causing marked ATP depletion; the second is the development of profound disturbances in membrane function. ATP depletion clearly contributes to the functional and structural consequences of ischaemia, and may also lead to membrane damage.

It is difficult to assess to what level ATP must drop, before irreversible ischaemia is obtained. Certainly previous research[7] found that ATP levels can drop to nearly 50% in chronic disease states, without morphological irreversible ischaemic changes, while an ATP decline to less than 40% were found in patients with end stage Multi-organ failure who later died. If we were therefore to extrapolate the results above and use 40% as a level consistent with irreversible ischaemia, this would correspond to an ATP concentration of 9.12 mmol/kg dw, equivalent to an intramuscular pH of approximately 6.65.

Thus, the pH results from the biopsy can be used to verify the accuracy of the pH readings from the pH monitor in the muscle tissue, and the damage sustained by skeletal muscle can be correlated with specific levels of ICP and pH.

RESULTS FOR EXAMPLE 6

The aim of this study was to demonstrate the ability to monitor the muscle pH changes associated with limb ischaemia, in both the acute and chronic forms. In vascular surgery there are a number of novel uses for pH monitoring including assisting in the decision to re-vascularise compromised limbs or to primarily amputate to avoid the potentially life threatening systemic effects of re-vascularisation.

The calibration, sterilisation and insertion techniques used in this study were identical to those used earlier. Markers were used in this instance during surgery for clamping of the artery (ON), release of the clamp (OFF), return to full circulation (CIRC) and in some cases, during the angiogram (ANGIO) used to check graft patency.

Figure 36:
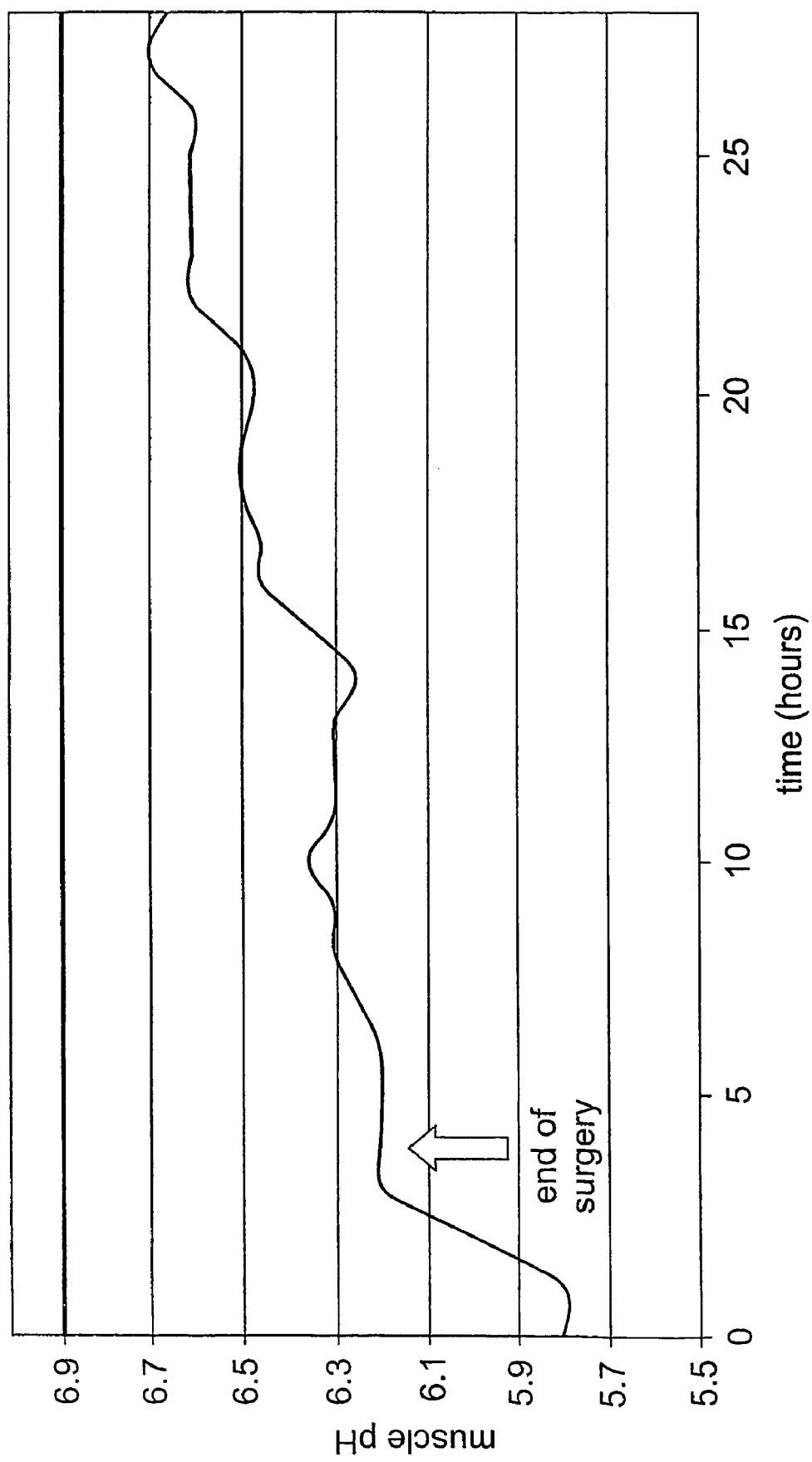
FIGS. 36 and 37 show graphs of muscle pH measured in a patient with acute on chronic ischaemia undergoing and recovering from femoral-popliteal bypass grafting.
Figure 37:
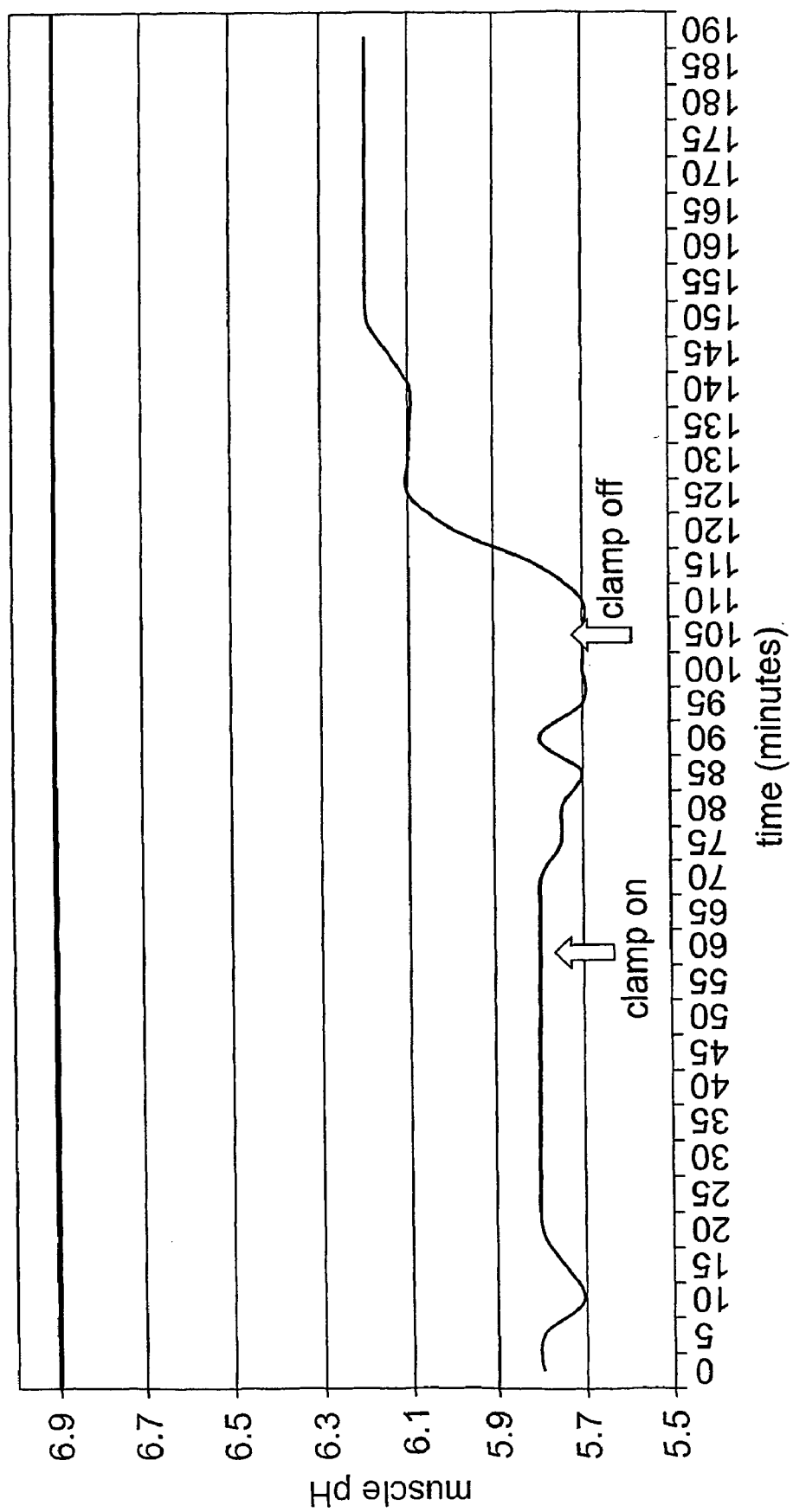
Figure 38:
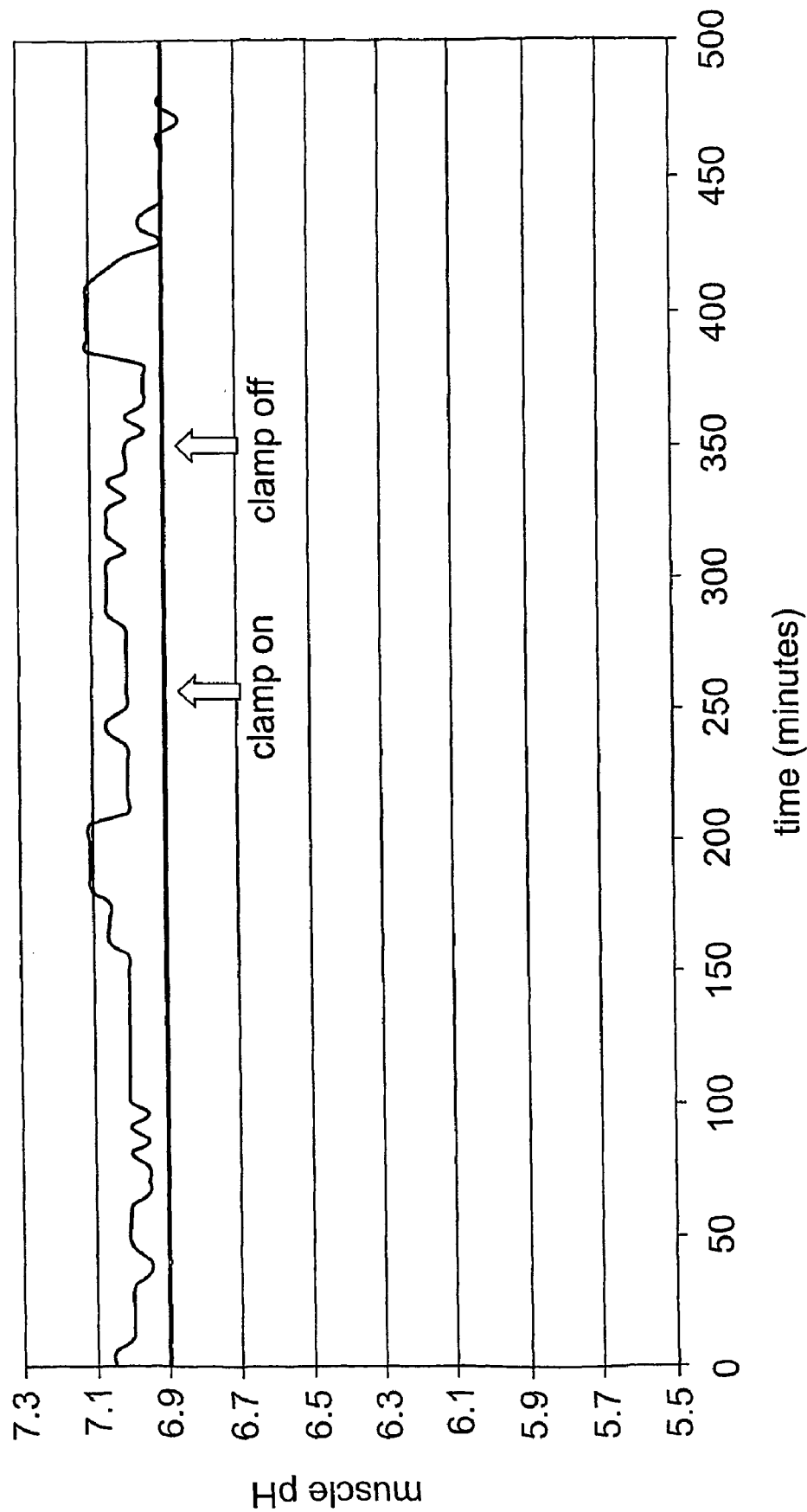
FIG. 38 shows similar data for another patient with chronic ischaemia.

Twelve patients fulfilled the ethical entry criteria and agreed to participate in the study. Of these 66% were male, and the mean age was 69 years. 33% were acute on chronic ischaemic limbs, the remainder were chronic cases. All underwent bypass procedures from the femoral artery to either the popliteal artery or distal vessels. Examples of the typical recordings of muscle pH gained are presented in FIGS. 36, 37 and 38. The chronic ischaemic limbs start within a normal physiological range of pH (6.9-7.2) and this decreases during surgery. On the other hand the patients with acute ischaemic events compounded by chronic limb ischaemic have a low muscle pH prior to bypass graft surgery, but in time this recovers as a result of recommencing the muscle circulation.

As with the previous examples, low muscle pH was associated with the symptoms and signs of muscle and nerve compromise. In the acutely ischaemic limbs, which started at pH of less than 6.4, each patient had numbness in their foot and weakness of foot dorsiflexion.

Patient X: Acute on Chronic Limb Ischaemia

An angiogram pre-operatively showed no blood supply going to the anterior compartment of the leg. He had weakness of dorsiflexion of the foot and great toe, and reduced sensation on the dorsum and sole of his foot. A starting pH of 5.8 indicates severe circulatory compromise in the anterior compartment. Following re-vascularisation, some immediate recovery is evident following removal of the vascular clamp (see FIG. 37), but this recovery continued for the next 24 hours (see FIG. 36). He continued to have signs of muscle and nerve damage following the recording period, but a degree of improvement was evident prior to terminating the muscle pH recording.

Patient Y: Chronic Limb Ischaemia

This lady had chronic ischaemia only, with collateral circulation present on angiogram pre-operatively. Throughout surgery, with the muscle in a resting state, the muscle pH remained within a normal physiological range (6.9-7.2). Despite clamping of the major blood vessel to the anterior compartment, little change was noted in the muscle pH (graph). This would suggest that the collateral circulation present was sufficient to maintain aerobic metabolism in muscle in a resting state. At no point during recording did the patient show signs of muscle or nerve compromise.

Modifications and improvements can be made without departing from the scope of the invention. For example, it is not necessary to use the pressure and pH monitors described here; other similar devices could be used.

The following disclosures referred to above are incorporated herein by reference:

1 Matsen F A. Compartment syndrome: A unified approach. *Clinical Orthopaedics* 1975; 113: 8.
2 Robinson C M, O'Donnell J, Will E, Keating J F. Dropped hallux after the intramedullary nailing of tibial fractures. *Journal of Bone and Joint Surgery (Br)* 1999; 81-B: 481-4.
3 Mars X, Hadley G P. Raised intracompartmental pressure and compartment syndromes. *Injury* 1998; 29; 403-411.
4 Whitesides T E, Haney T C, Morimoto K, Harada H. Tissue pressure measurements as a determinant for the need for fasciotomy. *Clinical Orthopaedics* 1975; 113: 43.
5 Heppenstall R B, Sapega A A, Scott R et al. The compartment syndrome. *Clinical Orthopaedics* 1988; 226: 138-155.
6 Willy C, Gerngross H, Sterk J. Measurement of Intracompartmental pressure with the use of a New Electronic Transducer-tipped Catheter System. *Journal of Bone and Joint Surgery (Am)* 1999, 81-A: 158-168.
7 Harris, R. C. and Hultman, E. (1992) Muscle phosphagen status studied by needle biopsy. In: Kinney J. M. and Tucker H N (Eds) Energy Metabolism: Tissue determinants and cellular corollaries. Raven Press, New York. pp 367-379; and Harris, R. C., Hultman, E. and Nordesjo, L.-O. Glycogen, Glycolytic Intermediates, and High-Energy Phosphates Determined in Biopsy Samples of Musculus Quadriceps Femoris of Man at Rest. Methods and Variance of Values. *Scand. J. clin. Lab. Invest.* 33, 109-120, 1974.
8 Olsen, C. An Enzymatic Fluorimetric Micromethod for the Determination of Acetoacetate, B-Hydroxybutyrate, Pyruvate and Lactate. *Clin. Chim. Acta.* 33, 293-300, 1971

The invention claimed is:

1. A method of diagnosing a pathological condition of a patient's body tissue, the method comprising determining the presence or severity of ischemia in the tissue by the steps of:
   inserting a pH sensor into the tissue;
   directly measuring intracompartmental pH in the tissue with the pH sensor and generating an electrical signal representative of the intracompartmental pH;
   converting, using a display, said electrical signal into intracompartmental pH values, and displaying, using said display, the intracompartmental pH values;

determining the presence or severity of ischemia and diagnosing the pathological condition using the intracompartmental pH values;

wherein the pH sensor consists of a single probe mounted on a catheter.

2. A method as claimed in claim 1, wherein the tissue is muscle.

3. A method as claimed in claim 1, wherein a second sensor is used to measure the intracompartmental pressure in the tissue.

4. A method as claimed in claim 1, wherein the catheter is inserted into a muscle through a cannula.

5. A method as claimed in claim 4, wherein the cannula is inserted into skeletal muscle in an orientation that is generally parallel to the muscle fibers.

6. A method as claimed in claim 4, wherein the cannula is inserted into a muscle adjacent to a bone fracture site, but not communicating with the bone fracture site.

7. A method as claimed in claim 1, wherein determining comprises:

determining the presence or severity of ischemia by comparing the intracompartmental pH values with a calibrated scale to determine the extent of tissue damage.

8. A method as claimed in claim 1, wherein the pathological condition is Acute Compartment Syndrome.

9. A method as claimed in claim 1, wherein the ischemia involves a shock selected from the group consisting of septic shock, neurogenic shock, cardiogenic shock and hypovolaemic shock.

* * * * *